(12) United States Patent
Hasumi

(10) Patent No.: US 8,076,132 B2
(45) Date of Patent: Dec. 13, 2011

(54) DENDRITIC CELL TUMOR INJECTION (DCTI) THERAPY

(75) Inventor: Kenichiro Hasumi, Suginami-Ku (JP)

(73) Assignee: Hasumi International Research Foundation, Washington, DC (US)

( * ) Notice: Subject to any disclaimer, the term of this patent is extended or adjusted under 35 U.S.C. 154(b) by 0 days.

(21) Appl. No.: 12/100,878

(22) Filed: Apr. 10, 2008

(65) Prior Publication Data

US 2009/0074713 A1  Mar. 19, 2009

(51) Int. Cl.
*A61K 35/12* (2006.01)
*A61K 38/20* (2006.01)
*A61K 38/21* (2006.01)
*A61P 35/00* (2006.01)

(52) U.S. Cl. .... 435/325; 424/85.2; 424/85.5; 424/93.71
(58) Field of Classification Search .................. 435/325; 424/85.2, 85.5, 93.71
See application file for complete search history.

(56) References Cited

U.S. PATENT DOCUMENTS

2004/0001829 A1* 1/2004 June et al. .................. 424/144.1
2006/0057120 A1* 3/2006 Bosch .......................... 424/93.7

OTHER PUBLICATIONS

Spisek et al. (Cancer Immunol. Immunther. 50:417-427 (2001)).*
Crammer et al. (Cancer Immunol. Immunther. 53:275-306 (2004)).*
Osada et al. (Inter. Rev. Immunol. 25(5/6):377-413 (2006)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Kumagi et al. (Inter. J. Oncol. 23:949-955 (2003)).*
Hashimoto et al. (Cancer Immunol. Immunother. 28(4):253-259 (1989); Abstract).*
Candido et al (Cancer Research, 2001, 61:228-236).*
Chi et al (J Immunother, Mar./Apr. 2005, 28:129-135).*
Sato et al (Cancer Immunol Immunother, 2004, 53:53-61).*

* cited by examiner

*Primary Examiner* — Lynn Bristol
(74) *Attorney, Agent, or Firm* — Eckert Seamans Cherin & Mellott, LLC; Carol A. Marmo, Esq.

(57) ABSTRACT

The invention relates to a method of treating tumor cells within a patient wherein immature dendritic cells developed from the patient's monocyte cells and a lymphocyte cultured medium (LCM) adjuvant are introduced into the patient directly into the patient's tumor cells. The immature dendritic cells and LCM adjuvant combine with the antigens in the tumor cells to form a cancer vaccine, thereby immediately treating the tumor cells of the patient. The invention also provides a precursor treatment step of treating the patient with radiation therapy or a chemotherapy regimen.

16 Claims, 18 Drawing Sheets

Protocol 1     Intra-tumoral Injection of imDC

Protocol 2     Intra-tumoral Chemotherapy Preceding imDC injection

*Rationale: Cytotoxic drugs may induced tumor cell lysis, antigen release and ablation of suppressor cells*

HITV Gastric Ca. Liver Meta (MM 72Y M)  Before (2004/06/04)  After (2004/11/02)

HITV Rec. of Rt. Breast Ca. Lt. Chest Wall & Mediastinal LN Meta. (YN 56F)

After (2005/03/14)

Before (2005/02/14)

DENDRITIC CELL TUMOR INJECTION (DCTI) THERAPY

CROSS REFERENCE TO RELATED APPLICATION

The present application is a continuation-in-part application to U.S. patent application Ser. No. 11/227,374, filed Sep. 15, 2005, now abandoned, which claims priority to U.S. Provisional Patent Application 60/610,822 filed Sep. 17, 2004, both of which are incorporated herein by reference.

BACKGROUND OF THE INVENTION

1. Field of the Invention

The present invention relates to a tumor therapy that includes the injection of immature dendritic cells and adjuvant directly into the patient's (a human or an animal) tumor tissue, which presents antigenicity as a vaccine antigen at the injection sight. Conjugation of these elements within the tumor tissue rapidly induce and activate the patient's immune system to dramatically reduce and/or eliminate tumor cells. Most adjuvants, which augment the immune response, can be directly injected with immature dendritic cells to the tumor tissue to achieve the reduction or elimination of tumor tissues.

2. Description of the Prior Art

Immunological adjuvants are used in combination with vaccines to augment the immune response to the antigen. One way in which immunological adjuvants function is by attracting macrophages to the antigen, so that the macrophages can present the antigen to the regional lymph nodes and initiate an effective antigenic response. Adjuvants may also act as carriers themselves for the antigen, or may influence the immune response by other mechanisms such as depot effect, cytokine induction, complement activation, recruiting of different cell populations of the immunological system, antigen delivery to different antigen presenting cells, regulation of the expression of HLA class I or class II molecules and the stimulation to produce different antibody subtypes. Many of the newer vaccines are only weakly immunogenic and thus require the presence of adjuvants.

Materials having adjuvant activity are well known. Alum ($Al(OH)_3$), and similar aluminum gels are adjuvants licensed for human use. The adjuvant activity of alum was first discovered in 1926 by Glenny (Chemistry and Industry, Jun. 15, 1926; J. Path. Bacteriol, 34, 267). Aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and, more recently, a HBsAg vaccine has been adjuvanted with alum.

One line of research in the development of adjuvants has been directed to the study of dendritic cells. Dendritic cells (DC) are professional antigen presenting cells (APC) that have the unique capacity to initiate primary immune responses in vivo and in vitro. They are derived from myeloid (DC1) or lymphoid (DC2) precursors and are distributed in their immature form throughout the body in tissues that commonly encounter environmental pathogens (skin, mucus membranes, gut epithelia, etc.). Whereas DC1 and DC2 comprise a small percentage of the total number of mononuclear cells in the peripheral circulation, DC1 precursors in the form of CD14+/CD11c+/HLA-DR+ monocytes are relatively abundant, constituting about 10% to 15% of mononuclear blood cells.

Immature DC express a host of surface structures that are involved in antigen acquisition, DC activation/maturation, and antigen presentation. Once DC encounter antigen, they undergo a maturation process characterized by the up-regulation of HLA class I and II molecules as well as co-stimulatory molecules and interact with cognate receptors on T and B lymphocytes, resulting in the generation of antigen specific cellular and humoral immune responses.

DC are considered to be the primary APC in the immune system. The ability to isolate these cells and/or their precursors and to study them in vitro has added considerable dimension to knowledge of their role in innate and acquired immunity. The classic means of generating human DC in vitro is to isolate and enrich CD14+-monocytes from peripheral blood and culture them for various periods of time in GM-CSF and IL-4 followed by final maturation with a number of cytokines, including IL-2, IL-6, IL-7, IL-13, IL-15, TNFα, IL-10, or with various other agents including lipopolysaccharides, PGE2, type 1 interferons, or double-stranded RNA.

Numerous investigators have shown that these in vitro generated monocyte-derived DC are potent antigen presenting cells (APC) capable of initiating primary and recall antigen-specific $CD4^+$ and $CD8^+$ T cell responses. Recent in vitro studies have generated a rather extensive body of information regarding the biology of DC1 and shed light on the processes whereby antigen specific immune responses are generated in vivo. In the peripheral tissues, immature DC acquire antigenic materials in the context of danger signals initiating a complex cytokine/chemokine milieu that is generated by DC and other cell types in the vicinity.

Soluble mediators produced by DC may act in an autocrine or paracrine fashion. T cells produce additional cytokines and chemokines following interaction with antigen armed DC, as do other immune cells that are activated by the cytokines released. This complex network of interactions may in turn create an environment that promotes the generation of DC from their monocyte precursors.

It is thought that those adjuvants which promote that maturation of dendritic cells, when administered in combination with a vaccine antigen, will result in more antigen presenting cells presenting the vaccine antigen to T lymphocytes and B cells, thus bolstering the immune response to the vaccine antigen. However, isolation of the most effective vaccine antigen has been extremely difficult since antigenicity of APC has always been subject to its evolution with antigenic drift and/or shift, and therefore many of the newer vaccines are only weakly immunogenic even though dendritic cells and adjuvant are present. The most effective vaccine antigen against the live tumor cells should be used with dendritic cells and adjuvant during a course of treatment to promote and to induce a rather strong immunogenicity.

SUMMARY OF THE INVENTION

The present invention solves the above need by providing the most effective antigenic vaccine antigen with dendritic cells and adjuvant to increase the amount and quality of the immune response against tumor cells.

In an aspect of the present invention, there is provided a method of reduction of tumor cells in tumor tissue of a patient, comprising collecting monocyte cells from the patient, culturing the monocyte cells with IL-4 and GM-CFS to form immature dendritic cells from the monocyte cells, and administering a therapeutically effective amount of the immature dendritic cells with a leukocyte cultured medium (LCM) adjuvant to the patient. The LCM adjuvant comprises at least three, preferably at least six and more preferably at least ten cytokines selected from eotaxin, FGF, G-CSF, GM-CSF, IFNγ, IP10, ILβ, IL1ra, IL2, IL4, IL5, IL6, IL7, IL8, IL9, IL10, IL12, IL13, IL15, IL17, MCP1, MIP1α, MIP1β, PDGFbb, RANTES, TNFα and VEGF.

The immature dendritic cells and LCM adjuvant are administered intratumorally, i.e., directly into the site of the tumor.

Optionally, this method provides treating the patient with chemotherapy, radiation or anti T-cell antibodies prior to the administration of the immature dendritic cells and LCM adjuvant.

In another aspect of the present invention, there is provided a method of reduction of tumor cells in tumor tissue comprising treating a tumor of a patient, with a chemotherapy regimen, collecting monocyte cells from the patient, culturing the monocyte cells with IL-4 and GM-CFS to form immature dendritic cells from the monocyte cells and administering a therapeutically effective amount of the immature dendritic cells with a leukocyte cultured medium (LCM) adjuvant to the patient. The LCM adjuvant comprises at least three, preferably at least six and more preferably at least ten cytokines selected from eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF.

Optionally, this method provides treating the patient with radiation prior to the administration of the immature dendritic cells and LCM adjuvant.

In a further aspect of the present invention, there is provided a method of reduction of tumor cells in tumor tissue comprising treating a tumor of a patient with a radiation therapy regimen, collecting monocyte cells from the patient, culturing the monocyte cells with IL-4 and GM-CFS to form immature dendritic cells from the monocyte cells, and administering a therapeutically effective amount of the immature dendritic cells with a leukocyte cultured medium (LCM) adjuvant into the tumor tissue of the patient. The LCM adjuvant comprises at least three, preferably at least six and more preferably at least ten cytokines selected from eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF.

Optionally, this method provides treating the patient with chemotherapy prior to the administration of the immature dendritic cells and LCM adjuvant.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

Figure 1:
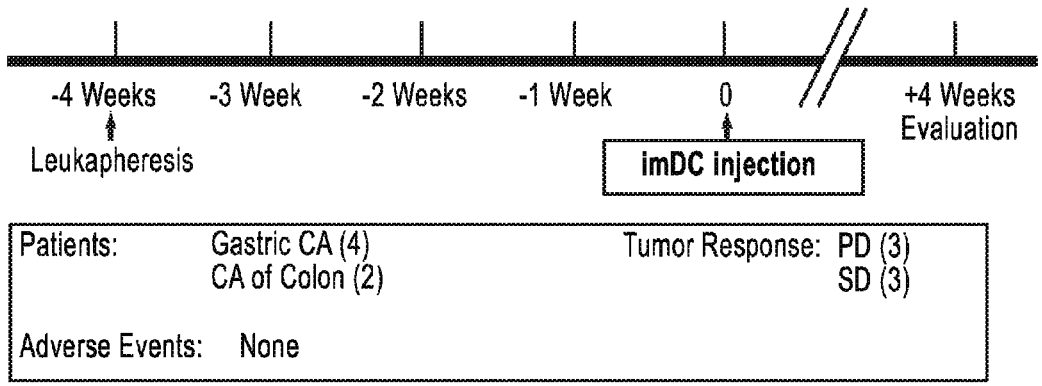
FIG. 1 shows two protocols for treating patients with tumors according to the methods of the present invention.
Figure 1:
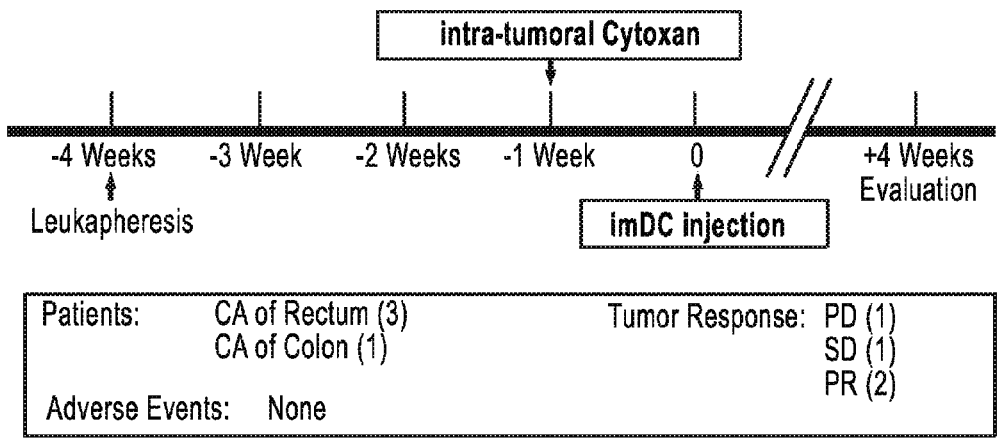
Figure 2:
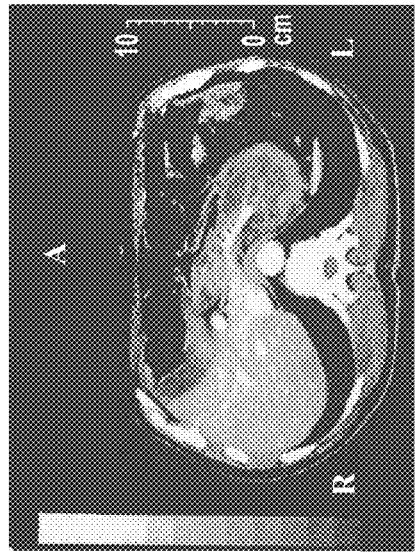
FIG. 2 shows a computerized tomography (CT) image of a patient with gastric cancer and liver metastasis before and after treatment according to the methods of the present invention.
Figure 2:
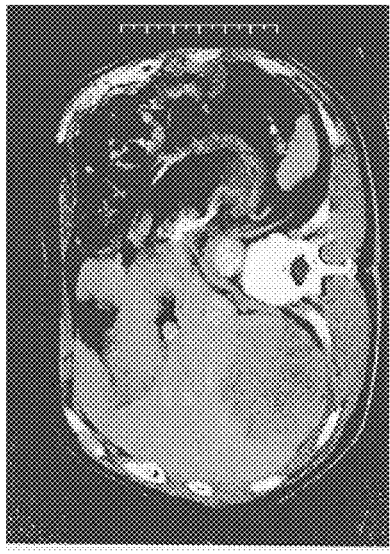
Figure 2:
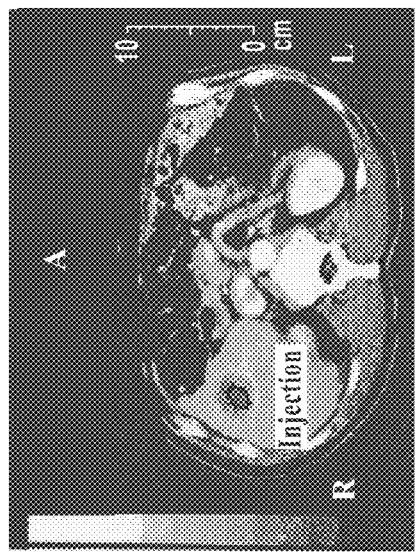
Figure 2:
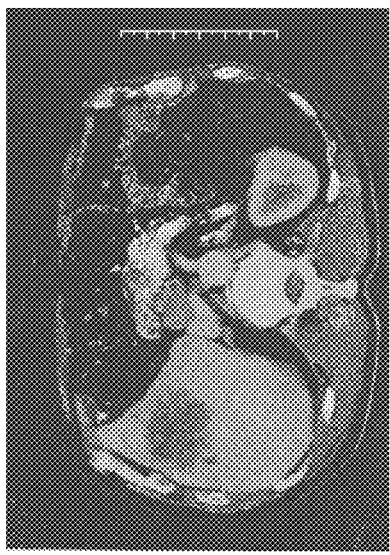
Figure 3:
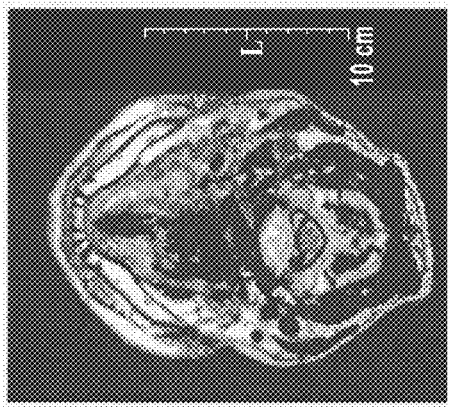
FIG. 3 shows a CT image of a patient with upper pharyngeal cancer before and after treatment according to the methods of the present invention.
Figure 3:
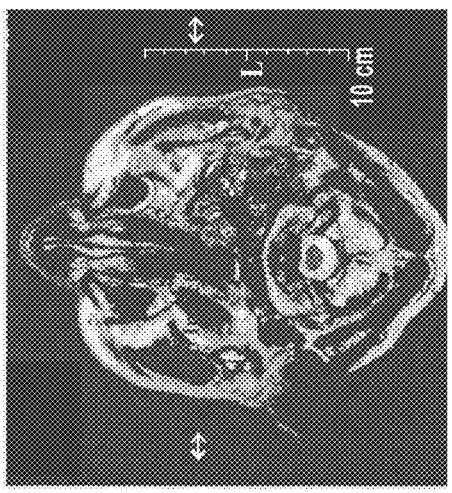
Figure 3:
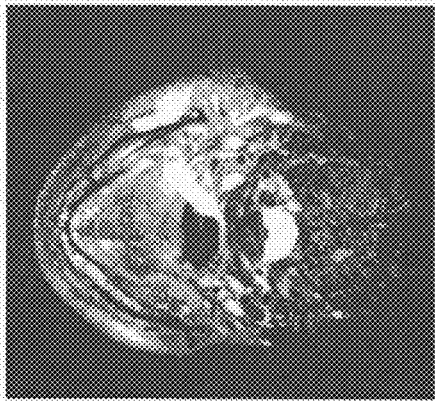
Figure 3:
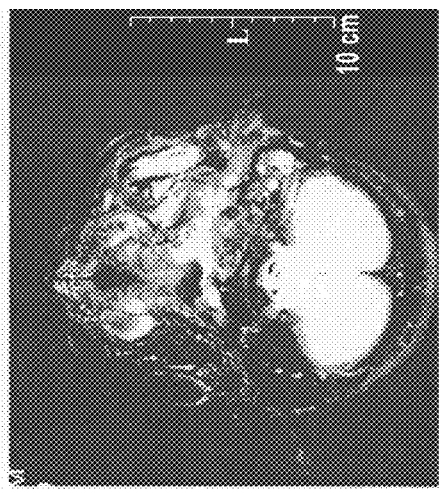

As used herein, the term "leukocyte cultured medium (LCM)" is synonymous and interchangeable with the term "activated leukocyte medium (ALM)."

As used herein, "patients" in clude mammals, which include humans.

As used herein, the term "therapeutically effective amount" refers to that amount of immature dendritic cells and lymphocyte cultured medium (LCM) adjuvant required to bring about a desired effect in a human or other mammal. In all instances, at its most basic level, the desired effect is a reduction of tumor cells in tumor tissue of the patient when compared to the tumor cells in the tumor tissue of the patient prior to employing the methods of the present invention.

The present invention provides treatment tumor tissue using full antigenic elements, which include antigenicity of both known and unknown antigen presenting cells, by locating them within the live tumor tissue in the human body (or alternatively, the body of an animal). This is in contrast to prior art cultured antigens obtained from tumor cell lines or any process added antigen, which have limited antigencity and outdated antigenic data or potency as a vaccine antigen for the patient's tumor cells. In particular, the present invention relates to a therapy that includes the injection of immature dendritic cells and adjuvant directly into the patient's tumor tissue, which presents antigenic elements as the vaccine antigen at the injection sight. The conjugation of these elements within the tumor tissue rapidly induce and activate the patient's immune system to dramatically reduce and/or eliminate tumor cells. Most adjuvants, which augment the immune response, can be directly injected with immature dendritic cells into the tumor tissue to achieve the reduction or elimination of tumor cells. Such adjuvants may include, without limitation, lipid-based, protein-based and polysaccharides-based adjuvants, such as lymphocyte cultured medium, Marignase, Agaricus, OK432, BCG, Lentinan (shiitake), Reishi, Sarunokoshikake, TNF Meshimakobu, Froint's complete or incomplete adjuvant, LPS, fatty acids, phospholipids, cytokines or a virus.

The present invention provides rapid reduction and/or elimination of tumor cells, which can be visually detected by MRI and/or CT and/or Echo scan within two weeks after the injection. The therapy according to a preferred embodiment of the invention includes the following steps: Step 1: Collecting peripheral blood monocyte cells (PBMC) from a patient; Step 2: Culturing these PBMC with GM-CFS and IL-4 to immature dendritic cells; Step 3: Injecting the cultured immature dendritic cells and an adjuvant into the tumor; and Step 4: Evaluating the tumor in two weeks.

In one particular embodiment, the effectiveness (immuno-response) of this method of treatment can be enhanced by pre-treating the tumor cells using known chemotherapy and/or radiation therapy techniques, which diminish the existing immune system, prior to steps 1-4 described above. In addition, the effectiveness (immuno-response) of this method of treatment can also be enhanced by injecting the tumors cells with an anti T-cell monoclonal antibody prior to steps 1-4 described above (either alone or in addition to the chemotherapy and/or radiation therapy described above).

EXAMPLES

The present invention is more particularly described in the following non-limiting examples, which are intended to be illustrative only, as numerous modifications and variations therein will be apparent to those skilled in the art.

Example 1

Treatment with Immature Dendritic Cells and Lymphocyte Cultured Medium Adjuvant

Six patients, four with stomach cancer and two with colon cancer, were used in this clinical investigation to assess the effect of intratumoral administration of immature dendritic cells (imDCs) with a lymphocyte cultured medium adjuvant (LCMadj). All patients were self-referred, had advanced cancers and progressive disease that had not responded to conventional standard therapies.
1. Methods Four weeks prior to administration of the imDC and LCM-adj, leukapheresis was performed on each patient to collect monocyte cells from the patient. The monocyte cells were cultured with IL4 and GM-CFS. This resulted in the production of imDCs. Four weeks later, a cocktail was prepared containing between about $10^7$ to $10^8$ imDCs and between about 1.0 to 2.0 mg of LCMadj to make up a 10% concentration in normal saline. Depending on the size of the tumor, between 2.0 to 50 cc of normal saline was injected into the tumor site of each patient. Four weeks after injection of the cocktail, the patients were evaluated by CT image analysis and measurement of serum tumor markers.
2. Results Of the six patients in this clinical study, three of the tumors of the patients showed stable disease (SD); defined as showing less than a 20% increase in tumor size and less than a 30% reduction in tumor size, with no increase in serum tumor markers. The tumors of the other three patients showed progressive disease (PD); defined as a 20% or greater increase in tumor size, new metastatic lesions and an increase in serum markers.

Example 2

Pretreatment with Chemotherapy Prior to Injection of Immature Dendritic Cells and Lymphocyte Cultured Medium Adjuvant Four patients, three with rectal cancer and one with colon cancer, were used in this clinical investigation to assess the effect of chemotherapy prior to intratumoral administration of imDCs with a LCMadj. All patients were self-referred, had advanced cancers and progressive disease that had not responded to conventional standard therapies.
1. Methods As shown in FIG. 1, Four weeks prior to administration of the imDC and LCMadj, leukapheresis was performed on each patient to collect monocyte cells from the patient. The monocyte cells were cultured with IL4 and GM-CFS. This resulted in the production of imDCs. Three weeks later, all patients were administered cytoxan intratumorally. One week later, a cocktail was prepared containing between about $10^7$ to $10^8$ imDCs and between about 1.0 to 2.0 mg of LCMadj to make up a 10% concentration in normal saline. Depending on the size of the tumor, between 2.0 to 50 cc of normal saline was injected into the tumor site of each patient. Four weeks after injection of the cocktail, the patients were evaluated by CT image analysis and measurement of serum tumor markers.
2. Results Of the four patients in this clinical study, two of the tumors of the patients showed a partial response (PR); defined as a 30% reduction in the size of the injected tumor, decline in serum markers, no increase in tumor size at other metastatic sites or appearance of new metastasis. The tumor from the third patient showed stable disease (SD), as defined above; and the tumor from the fourth patient showed progressive disease (PD), as defined above.

Example 3

Injection of Immature Dendritic Cells and Lymphocyte Cultured Medium Adjuvant or Pretreatment with Chemotherapy or Radiation Therapy Prior to Injection of Immature Dendritic Cells and Lymphocyte Cultured Medium Adjuvant Twenty patients with advanced malignancies of different types were used in this clinical study to assess the effect of intratumoral administration of imDCs with an LCMadj, chemotherapy prior to imDCs and LCMadj administration or radiation therapy prior to imDCs and LCMadj administration. All patients were self-referred, had advanced cancers and progressive disease that had not responded to conventional standard therapies. 1.
Methods Four weeks prior to administration of the imDC and LCM-adj, leukapheresis was performed on each patient to collect monocyte cells from the patient. The monocyte cells were cultured with IL4 and GM-CFS. This resulted in the production of imDCs. Three weeks later, three patients received radiation therapy and 11 patients were given chemotherapy (see Table 1) by administering the chemotherapeutic agent intratumorally. One week later, a cocktail was prepared containing between about $10^7$ to $10^8$ imDCs and between about 1.0 to 2.0 mg of LCMadj to make up a 10% concentration in normal saline. Depending on the size of the tumor, between 2.0 to 50 cc of normal saline was injected into the tumor site of each patient. Four weeks after injection of the cocktail, the patients were evaluated by CT image analysis and measurement of serum tumor markers.

2. Results

Figure 4:
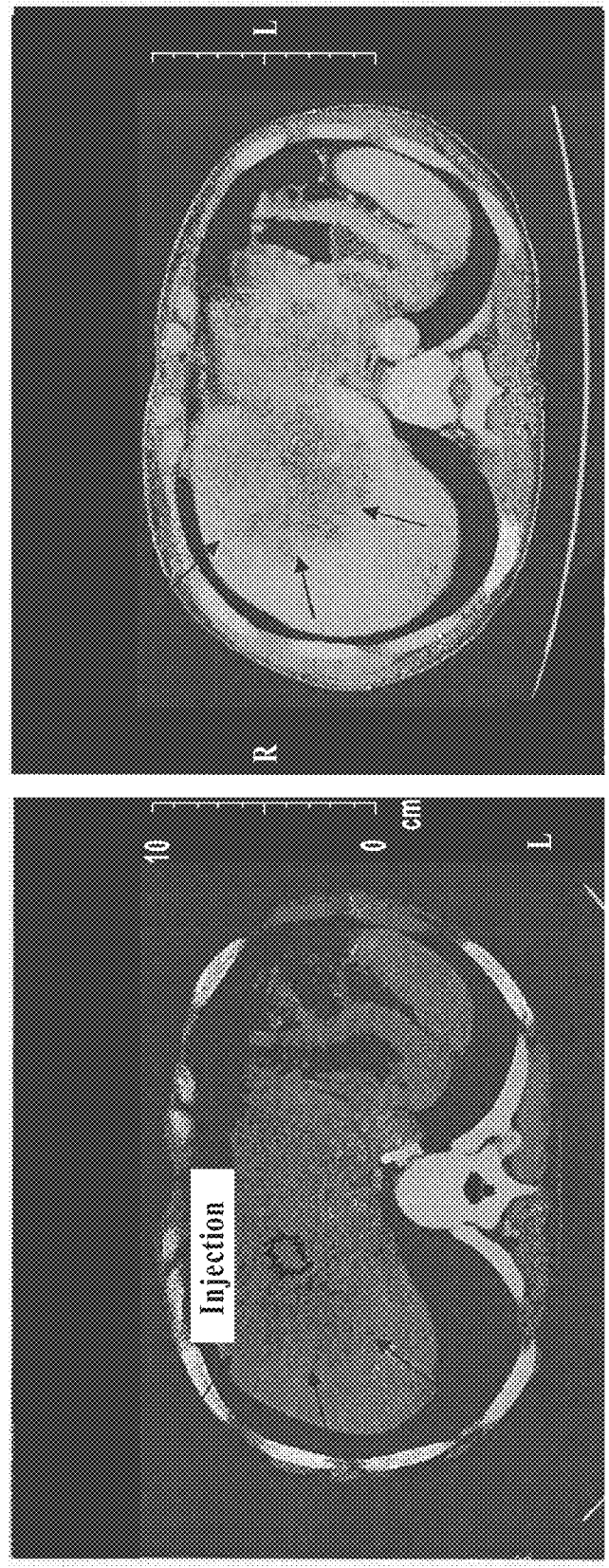
FIG. 4 shows a CT image of a patient with sigmoid cancer and liver metastasis before and after treatment according to the methods of the present invention.
Figure 5:
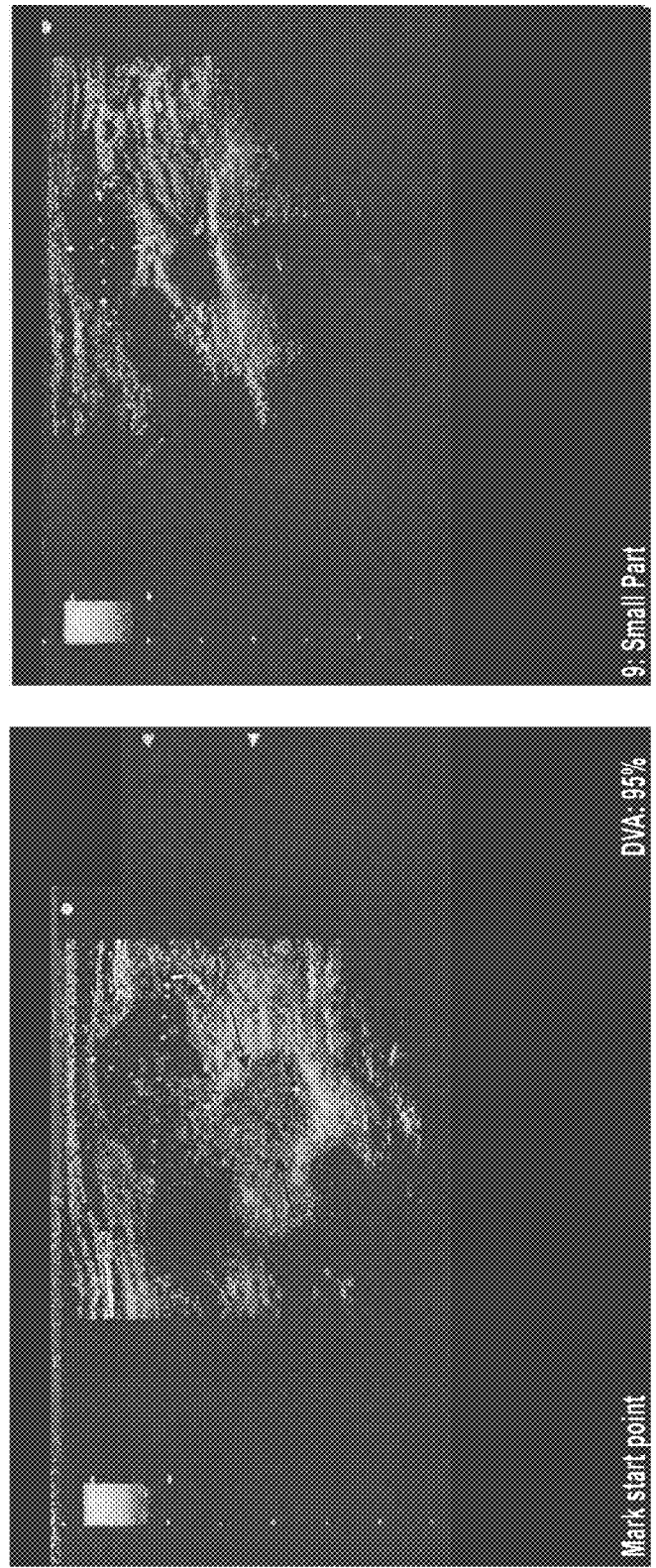
FIG. 5 shows a CT image of a patient with rectal cancer and lung, pelvic and left cervical metastasis before and after treatment according to the methods of the present invention.
Figure 6:
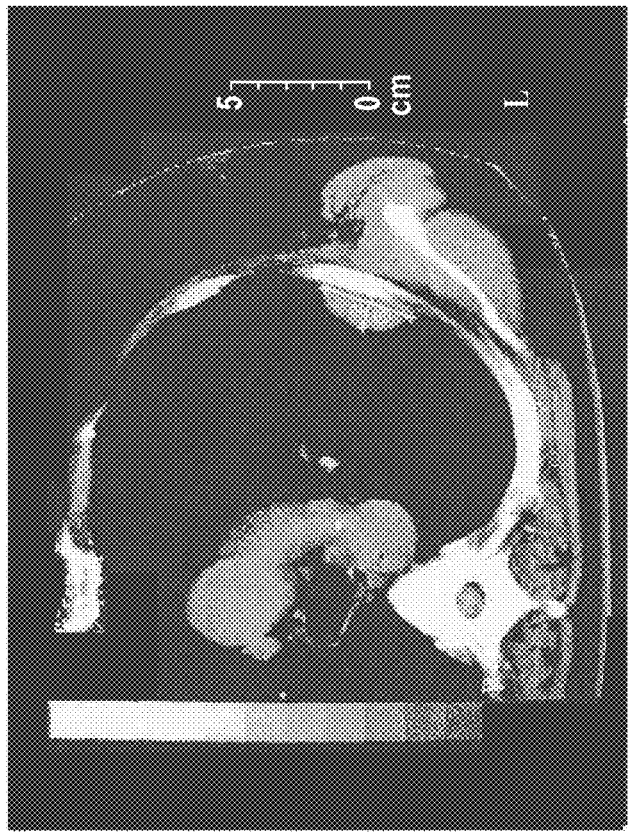
FIG. 6 shows a CT image of a patient with right breast cancer and left chest wall and mediastinal metastasis before and after treatment according to the methods of the present invention.
Figure 6:
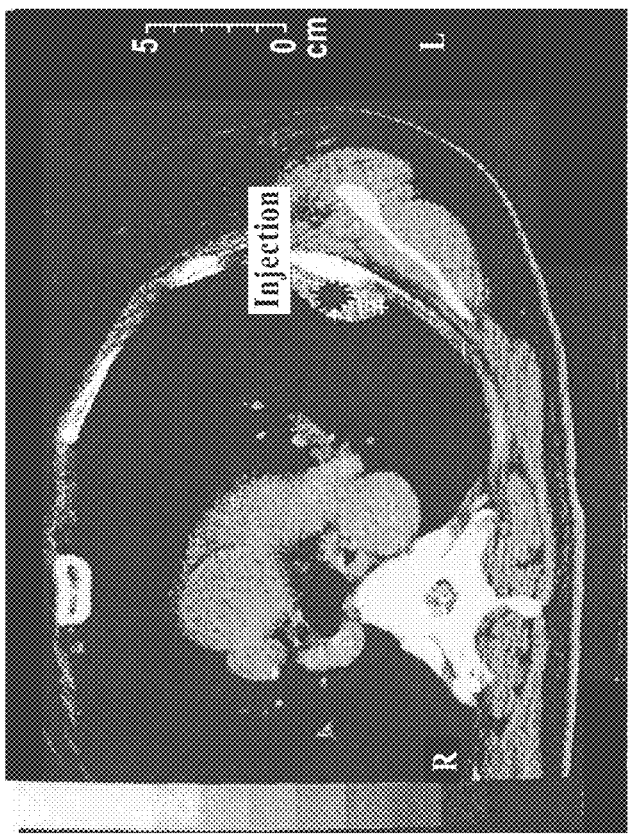

As shown in Table 1, of the six patients that did not receive any prior treatment before administration of the imDCs and LCMadj cocktail, the tumors of two patients showed a partial response (PR) (see, for example, FIG. 2); the tumors of two other patients showed no change (NC) from their previous condition (see, for example, FIG. 3); and the tumors from two other patients showed progressive disease (PD) (see, for example, FIG. 4). Of the three patients that had radiation therapy prior to administration of the imDCs and LCMadj cocktail, the tumor from one patient showed no change (NC) from its previous status. The other patient dropped out before they could be evaluated. Of the eleven patients that received chemotherapy prior to administration of the imDCs and LCMadj cocktail, the tumors from three of the patients showed a partial response (PR) (see for example FIG. 5); the tumors from six of the patients showed no change (NC) from their previous condition (see, for example, FIG. 6); and the tumors from two patients showed progressive disease (PD). FIGS. 2-7 show CT images of various cancers and their response to the treatment protocol.

TABLE 1

| Sex | ID | Diagnosis | Stage | Pre-treatment | Evaluation |
|---|---|---|---|---|---|
| F | 030593 | Gastric Ca Op Liver Meta | Rec | No | PR |
| M | 011077 | Epi pharyngeal Ca Op | Rec | No | NC |
| M | 040231 | Sigmoid Ca Op Liver, Lung & Urinary Bladder Meta | Rec | No | PD |
| M | 040265 | Gastric Ca Op Peritoneal Meta | Rec | No | NC |
| M | 051585 | Gastric Ca Op Mult, Lever Meta | Rec | No | PR |
| M | 040402 | Rt. Lung Ca Op Rt Chest Wall Meta | Rec | Radiation | Drop Out |
| M | 040465 | Gastric Ca Op Liver Meta | Rec | Radiation | NC |
| F | 040865 | Malig. Melanoma of Gingiva Op Cervical LN Meta | Rec | Endoxan | PR |
| F | 031180 | Rectal Ca Op., Lung Meta Pelvic & Lt. Cervical LN Meta | Rec | Endoxan | PR |
| F | 040764 | Sigmoid Ca Op Mult. Liver Meta | Rec | Chemo (TAI) | NC |
| F | 010863 | Rec. of Rectal & Caecal Cancer Op., Lt. Cervical LN Meta | Rec | None | PD |
| F | 041095 | Rectal Ca Op. Lung Meta Pelvic LN Meta | Rec | Radiation | NC |
| F | 040924 | Breast Ca Op Skin Meta | Rec | Endoxan | PR |
| F | 040520 | Breast Ca Op Skin Meta | Rec | Endoxan | NC |
| F | 031119 | Lt. Pylvic Tumor Op. Lt. Cervical & Axilla LN Meta | Rec | Endoxan | PD |
| F | 040558 | Rec. of Rt. Breast Cancer Op., Liver Metastasis | Rec. | CDDP | NC |
| M | 040325 | Malig. Mesothelioma | IV | Endoxan | NC |
| M | 041266 | Rectal Ca Op Liver Metastasis | Rec | Endoxan | PD |
| F | 900182 | Rt. Breast Ca Op., Lt. Chest Wall & Medistinal LN Meta | Rec | CDDP | NC |
| F | 041264 | Rec. of Endometrial Cancer op., Pelvic LN Metastasis | Rec | CDDP | NC |

3. Discussion

Approximately 80% of the patients showed some degree of tumor regression. Moreover, none of the patients had any adverse reaction to the treatment protocol they were given. In those patients showing tumor regression, this was evident within one month after completion of the treatment protocol and effectiveness of the treatment was observed after over 3 months. The number of cases and percentage effectiveness of the treatment protocols were as follows:

Complete response (CR); defined as a decrease in serum markers to normal levels, complete disappearance of all measurable lesions: 0 (0%)

| | |
|---|---|
| PR | 5 (26%) |
| NC | 10 (53%) |
| PD | 4 (21%) |

Example 4

Preparation of Lymphocyte Cultured Medium (LCM) for Clinical Application

Objective

To develop a clinically acceptable method for the production of LCM from elutriated cell fractions obtained from mononuclear cells (MNC) and generate preliminary data in support of a potential ND submission.

BACKGROUND

A variety of cytokines are known to induce the differentiation and maturation of monocyte-derived dendritic cells (DC). Soluble factors found in cell-free supernatants from monocyte and anti-CD3-activated T cells have been found to increase the expression of activation and maturation markers. In this laboratory, earlier studies showed that activation of ficolled PBMC with anti-CD3/CD28 beads results in a product that could mature APCs and augment T cell responses. The activated lymphocyte medium contained a mix of cytokines and chemokines known to be important for the development and migration of DC including GM-CSF, TNFα, IFNγ, IL8, MCP-1 and MIP1. When cultured in LCM, purified monocytes and monocytes in whole PBMC preparations developed a DC-like phenotype characterized by the loss of CD14 and upregulation of costimulatory molecules. Immature DC exposed to LCM underwent maturation within 48 h marked by an increase in surface expression of CD40, CD80, CD86, CD83 and HLADR. LCM-treated DC stimulated potent allogeneic PBMC responses and boosted antigen-specific T cell responses to antigens. Enhanced T cell and antibody responses were observed when LCM was co-administered with a variety of vaccines in macaques. LCM represents a potential 'physiologic' product for the generation of DCs in vitro as well as vaccine adjuvant; providing a cytokine milieu for DC generation and immune activation in vivo. Data using activated PBMCs as well as activation products developed from elutriated lymphocyte fractions are included in this study.

The cytokine composition of LCM is shown in Table 2.

TABLE 2

Quantities of Cytokines or Chemokines (PBMCs)

| | Quantity (pg/ml) |
|---|---|
| GM-CSF | 23000 |
| IFNα | 0 |
| IFNγ | 31000 |
| IL1β | 70 |
| IL2 | 5900 |
| IL3 | 1000 |
| IL4 | 280 |
| IL6 | 2170 |
| IL8 | 47970 |
| IL10 | 660 |
| IL12 | 10 |
| IL15 | 0 |
| MCP1 | 110040 |
| M-CSF | 8690 |
| MIP1α | 127200 |
| MIP1β | 157890 |
| PGE2 | 1540 |
| RANTES | 20640 |
| CD40L | 1270 |
| SDF1α | 0 |
| TGFβ | 0 |
| TNFα | 6430 |

Figure 7:
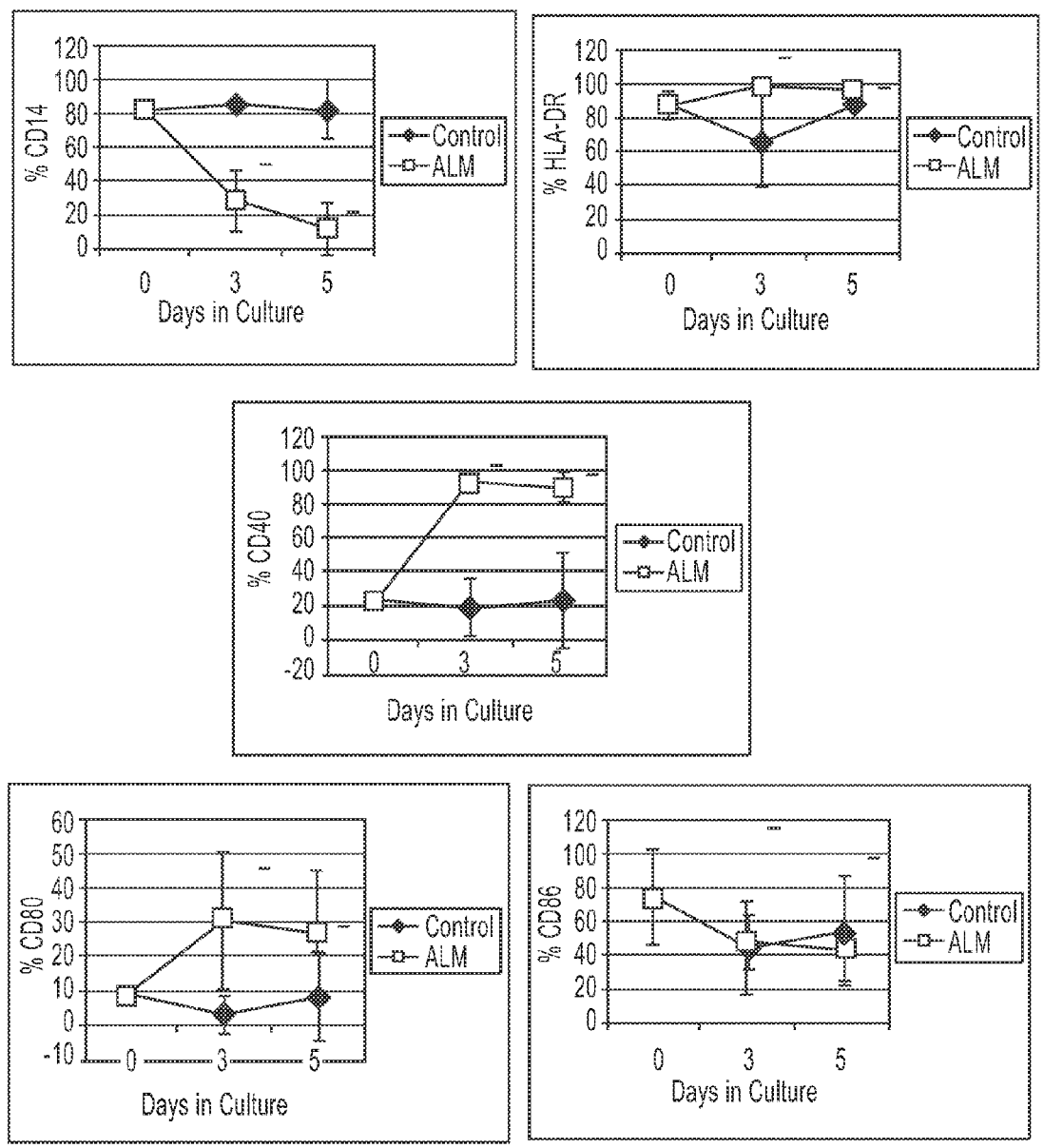
FIG. 7 shows the effect of LCM on surface marker expression, in which monocytes in PBMCs differentiate to a DC-like phenotype following exposure to LCM.
Figure 8:
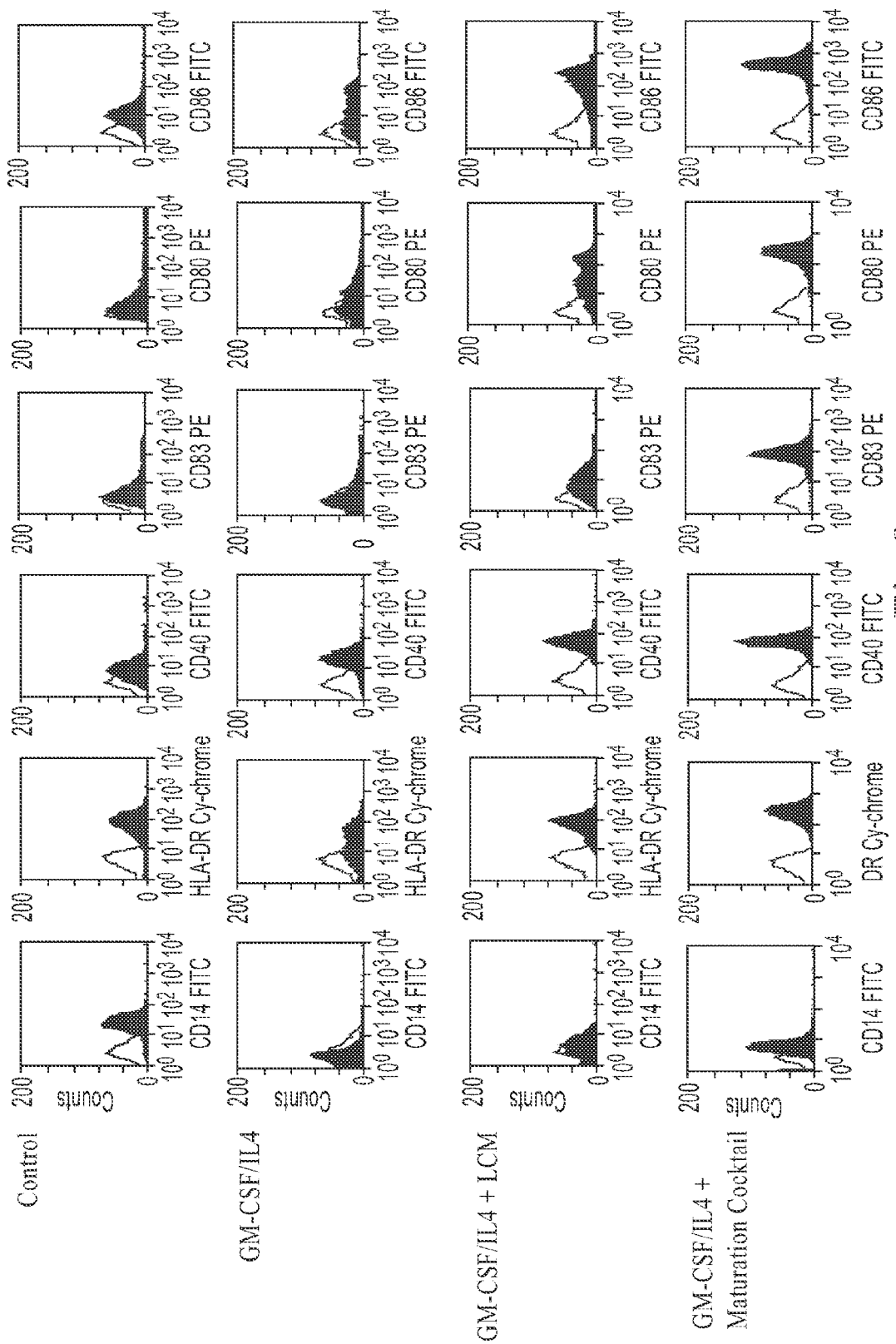
FIG. 8 shows the effect of LCM on surface marker expression, in which immature monocyte-derived DCs differentiate to a mature-phenotype following exposure to LCM.

FIGS. 7 and 8 show the effect of LCM on surface marker expression. Regarding FIG. 7, monocytes in PBMCs differentiated to a DC-like phenotype following exposure to LCM. Expression of CD14, HLA-DR, CD40, CD80, and CD86 was analyzed at 0, 3 and 5 days following exposure to LCM. Data represent mean±SEM of 11 experiments and  indicates $p<0.005$. Regarding FIG. 8**, immature monocyte-derived DCs differentiated to a mature-phenotype following exposure to LCM. Elutriated monocytes were cultured with GM-CSF/IL-4 for 3-4 days followed by addition of media alone, LCM or Maturation Cocktail for 48 hours. Monocytes cultured in cRPMI only were used as a negative control. CD11c+DCs were examined for surface expression of CD14, HLA-DR, CD40, CD83, CD80, and CD86 by flow cytometry. Open histograms represent staining of DC with isotype control mAb, and shaded histograms represent staining of DC with specific mAb.

Figure 9:
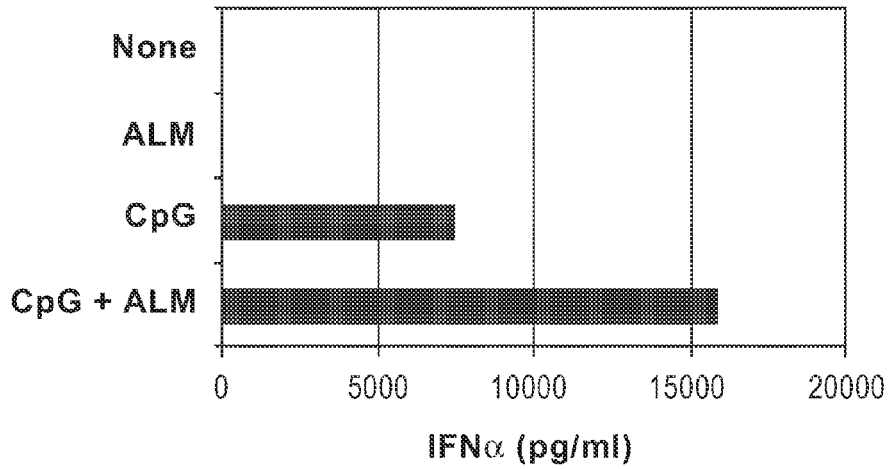
FIG. 9 shows that LCM augments CpG-induced maturation and IFNα production by CpG treated plasmacytoid DCs (pDCs)
Figure 9:
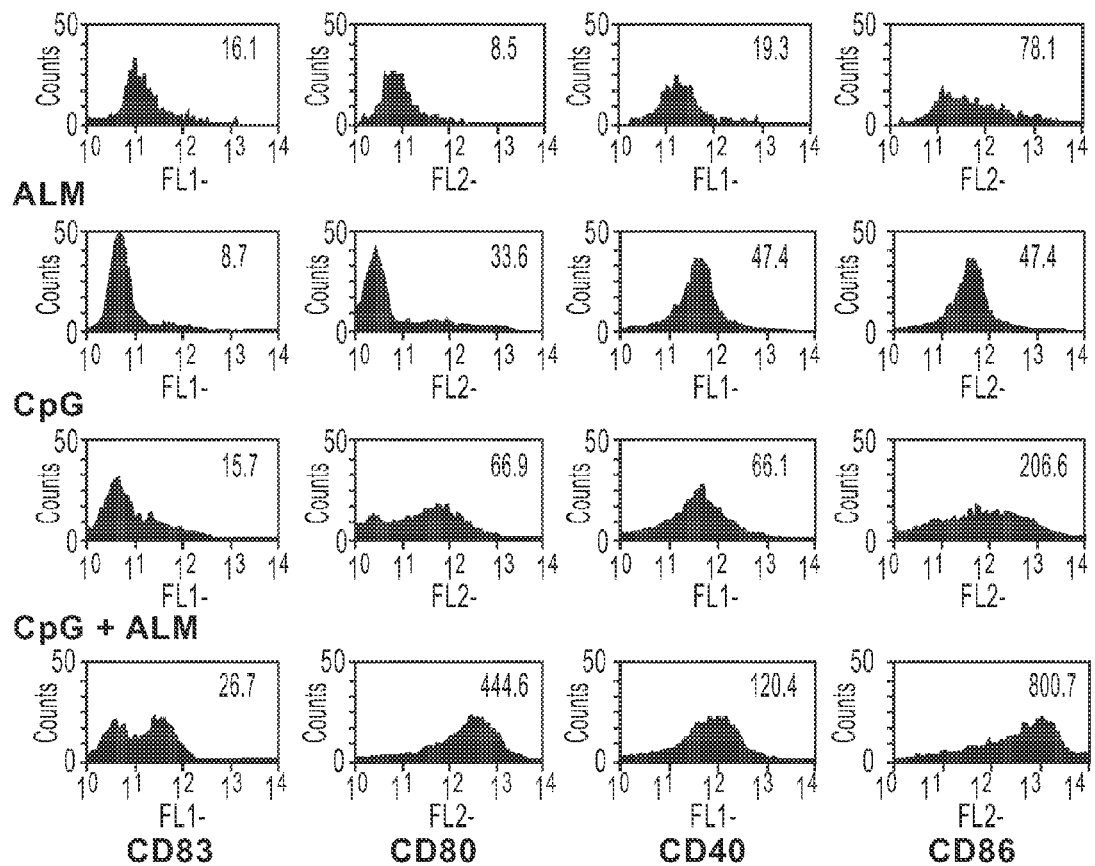

FIG. 9 shows that LCM augments CpG-induced maturation and IFNα production by CpG treated plasmacytoid DCs (pDCs). Human pDCs (91-96% purity assessed by surface expression of CD123) were isolated using positive BDCA-4 immunomagnetic selection (Miltenyi Biotech, Auburn, Calif.). Typically, $1\times10^8$ monocytes yielded $3\text{-}4\times10^5$ pDCs. The pDCs were adjusted to $0.5\times10^6$ cells/ml in DMEM (Life Technologies, Rockville, Md.) containing 10% fetal bovine serum (BioWhittaker, Walkersville, Md.) and cultured at $1\times10^5$ cells per well in 96 well round bottom plates. Freshly isolated pDCs expressed an immature phenotype (CD83⁻, low MHC and co-stimulatory molecules). pDCs were matured with CpG2006 (20 µg/ml) for 24 to 48 h. LCM was added at a 25% dilution.

Figure 10:
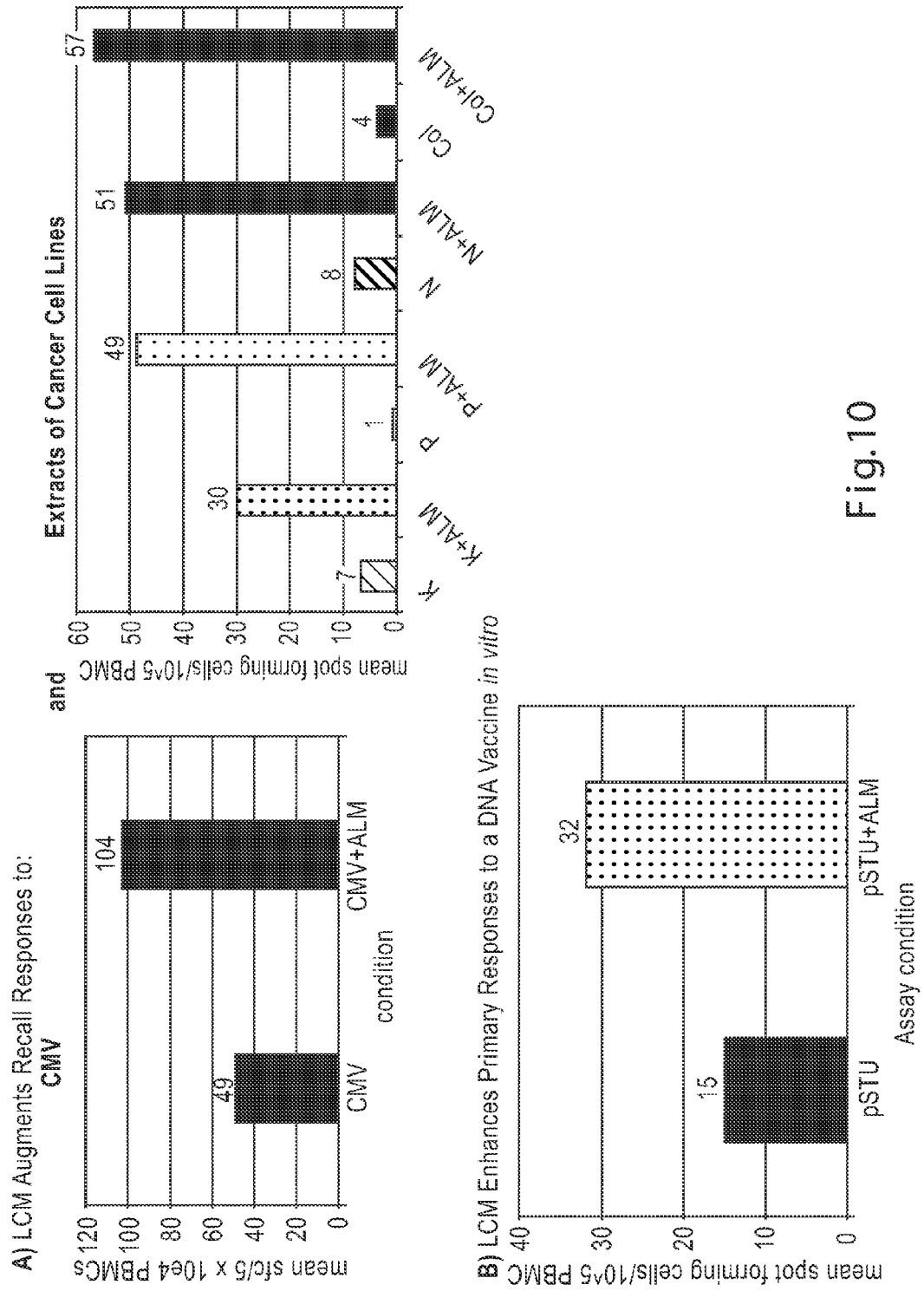
FIG. 10 shows the effect of LCM treatment on T cell responses in vitro.

FIG. 10 shows the effect of LCM treatment on T cell responses in vitro. PBMCs were cultured for 24 h with or without antigen and/or LCM (25%), washed to remove LCM and plated for: (A) Recall Responses (re-plated on ELISPOT for 24 hours; (B) Primary Responses (culture for 7 days with media containing IL7 and IL15, cells washed, then replated on ELISPOT with antigen for 24 hours). CMV=cytomegalovirus lysate; cancer cell lines: K=gastric cancer, P=pancreatic cancer, N=renal cell carcinoma, col=colon cancer.

Effect of LCM Immunization with Vaccines on T Cell and Antibody Responses-In Vivo.

Total solubilized protein was measured in pooled LCM samples (BioRad protein assay based on the method of Bradford, absorbance at 595 nm). To determine adjuvant activity of LCM in vivo, 0.3 ml LCM (97.5 ng) was mixed with individual vaccines (hepatitis A=HepA; tetanus diphtheria toxoid=TDT; rabies or prostate specific antigen=PSA) and each vaccine/LCM mixture was injected IM in macaques at four separate sites (right and left arms and thighs). Selected cytokine levels are calculated in Table 3.

TABLE 3

Cytokine/Chemokine Concentrations of Pooled LCM Injected into Macaques

| | ng/ml | ng/injection site | total ng/injection |
|---|---|---|---|
| GM-CSF | 310 | 93 | 372 |
| IL-4 | 2.5 | 0.75 | 3 |
| IL-5 | 1.5 | 0.45 | 1.8 |
| IL-8 | 4.3 | 1.29 | 5.2 |
| IL-10 | 3.2 | 0.96 | 3.8 |
| MCP-1 | 3.7 | 1.11 | 4.4 |
| IL-1α | 0.228 | 0.07 | 0.274 |
| IL-1β | 0.364 | 0.11 | 0.437 |
| IL-12p40 | 0.313 | 0.09 | 0.376 |

Animals were injected with vaccines alone or vaccines plus LCM and cell and serum samples removed for testing according to the following timeline, shown in Table 4.

TABLE 4

Treatment timeline for animals receiving vaccine or vaccine plus LCM

| Treatment | | 0 | 7 | 14 | 21 | 28 | 35 | 42 | 49 | 56 |
|---|---|---|---|---|---|---|---|---|---|---|
| | | Days of injection | | | | | | | | |
| Vaccine alone | HepA | + | + | + | | | | | | |
| | TDT | + | + | + | | | | | | |
| | Rabies | + | + | + | | | | | | |
| | PSA | + | + | + | | | | | | |
| | | Days samples collected for testing | | | | | | | | |
| | Cells (ELISPOT) | + | | | | + | + | + | + | |
| | Serum (ELISA: IgG antibodies to HLA class I and HLA class II antigens and vaccines) | + | | | | + | + | + | + | |
| Vaccine + LCM | HepA | + | + | + | | | | | | |
| | TDT | + | + | + | | | | | | |
| | Rabies | + | + | + | | | | | | |
| | PSA | + | + | | | | | | | |
| | Cells (ELISPOT) | + | + | + | + | + | + | + | + | |
| | Serum (ELISA: IgG antibodies to HLA class I and HLA class II antigens and vaccines) | + | + | + | + | + | + | + | + | |

+ = procedure done on indicated day

Figure 11:
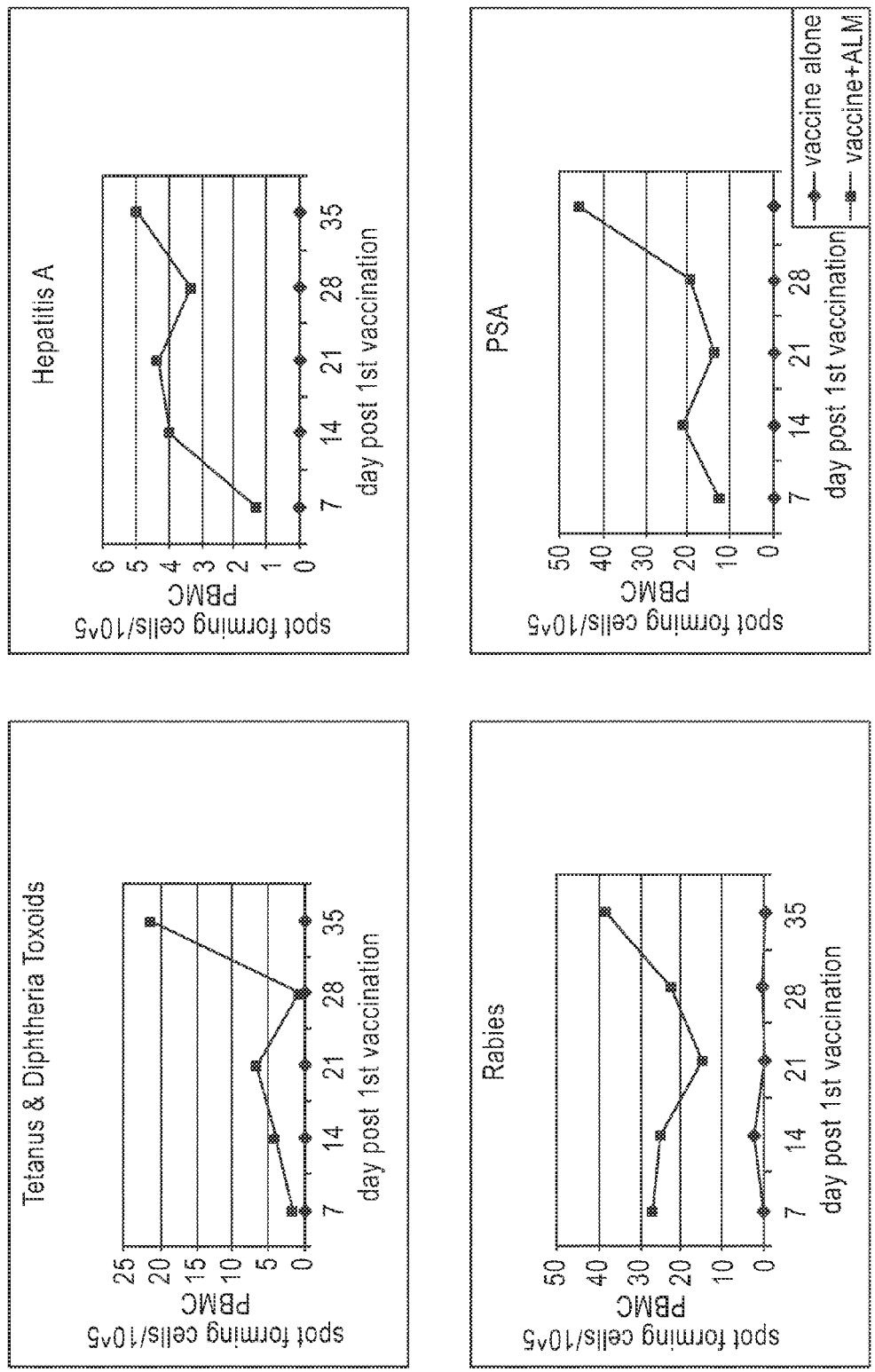
FIG. 11 shows T cell responses to vaccines are enhanced following treatment with LCM (ELISPOT)
Figure 12:
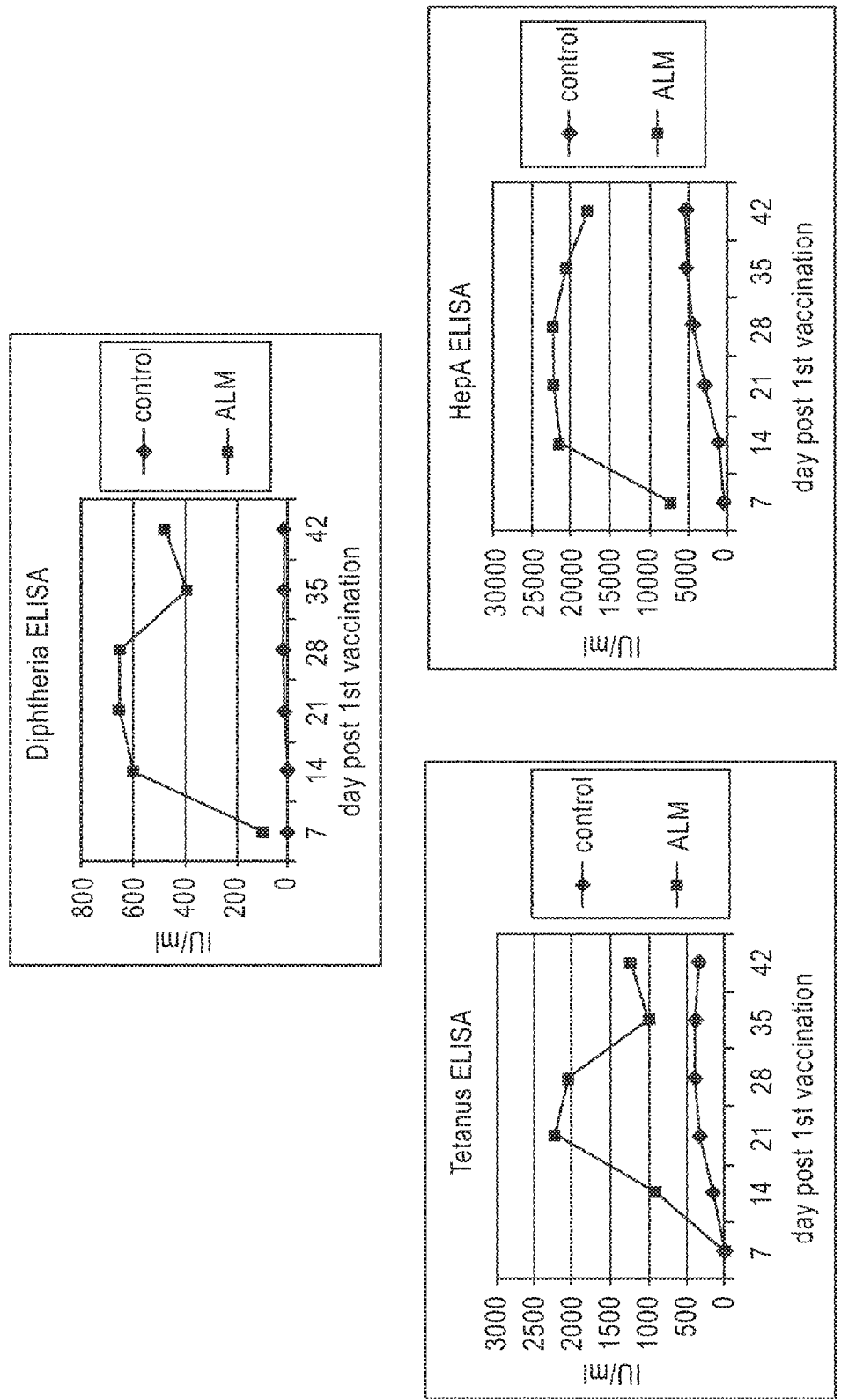
FIG. 12 shows antibody responses to vaccines are enhanced following treatment with LCM (ELISA)
Figure 13:
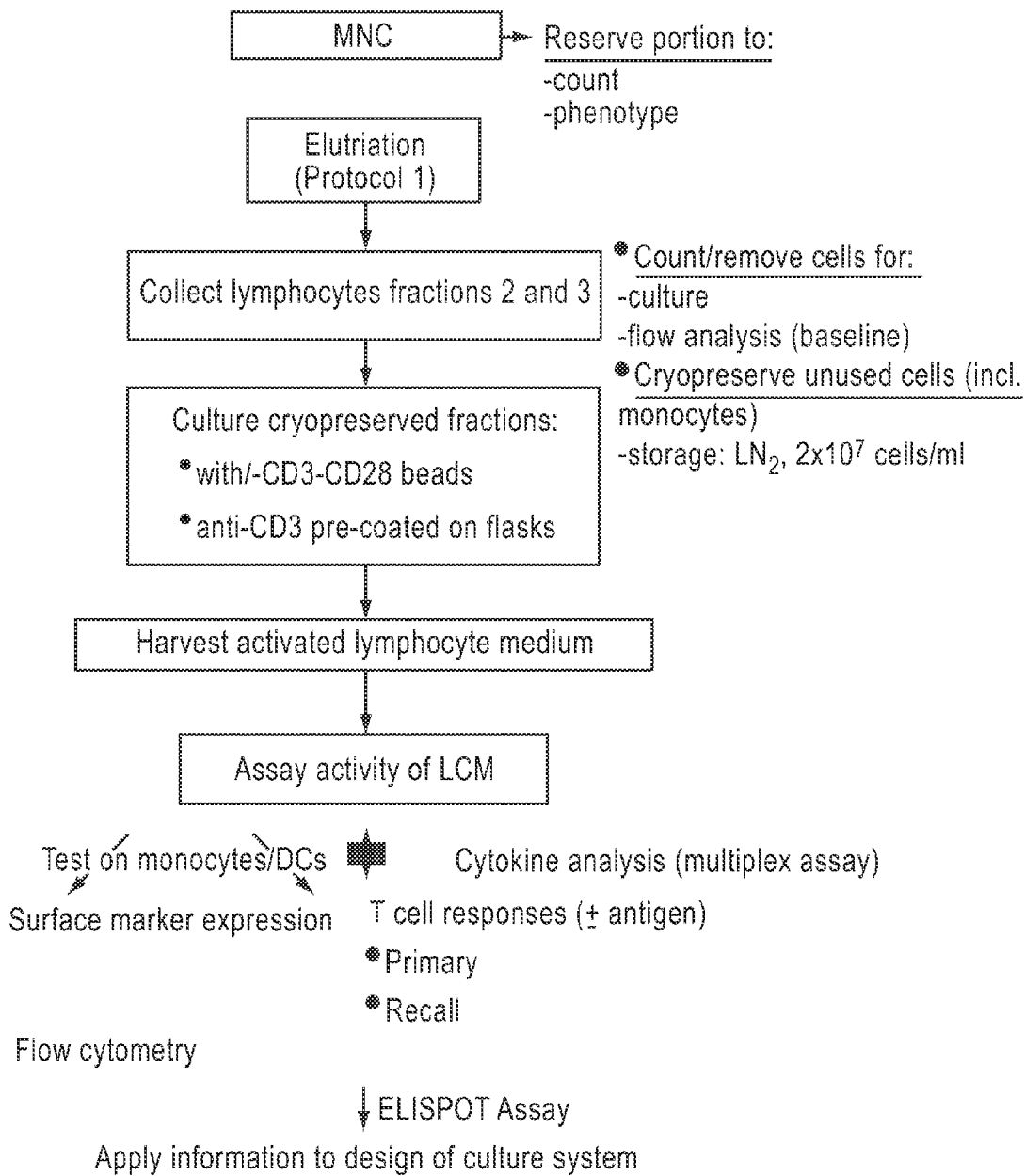
FIG. 13 provides an outline of an elutriation study.

FIG. 11 shows that T cell responses to vaccines were enhanced following treatment with LCM (ELISPOT). FIG. 12 shows that antibody responses to vaccines were enhanced following treatment with LCM (ELISA).

Table 5 shows detection of HLA Ab in Macaque serum using solid phase ELISA.

TABLE 5

| Monkey ID code | Class I | | | | | | | | | Class II | | | | | | | | |
|---|---|---|---|---|---|---|---|---|---|---|---|---|---|---|---|---|---|---|
| Day of serum collection | 0 | 7 | 14 | 21 | 28 | 35 | 42 | 49 | 56 | 0 | 7 | 14 | 21 | 28 | 35 | 42 | 49 | 56 |
| Vaccine only | | | | | | | | | | | | | | | | | | |
| CC8A | − | | | | | − | − | − | − | | | | | | − | − | − | − |
| CG33 | − | | | | | − | − | − | − | | | | | | − | − | − | − |
| 98021 | − | | | | | − | − | − | − | | | | | | − | − | − | − |
| 99E030 | − | | | | | − | − | − | − | | | | | | − | − | − | − |
| 99061 | − | | | | | − | − | − | − | | | | | | − | − | − | − |
| Vaccine and LCM | | | | | | | | | | | | | | | | | | |
| LCM-98023 | − | − | − | − | + | + | + | + | + | − | − | − | − | − | − | − | − | − |
| LCM-99E145 | − | − | − | − | − | − | − | − | − | − | − | − | − | − | − | − | − | − |
| LCM-99E107 | − | − | + | + | + | + | + | + | + | − | − | − | − | − | − | − | − | − |

*GTI, Waukesha, WI;
+ = positive detection,
− not detected

Summary: Media from Anti-CD3/CD28 Activated PBMCs:

Contain cytokines and chemokines that are known to influence the generation of immune responses; induces maturation and differentiation of monocyte-derived DCs and pDCs; augments primary and recall antigen specific T cell responses in vitro; and augments antibody and T cell responses to vaccines in non-human primates.

Data Generated from 'Purified' Elutriated Lymphocyte-Derived LCM

To determine if LCM production could be adapted to a larger scale process potentially better defined and more easily amenable to FDA guidelines than the use of ficolled whole blood PBMCs, a study on apheresed cells with autologous testing was initiated. MNC were fractionated into different cell types from healthy individuals utilizing a programmable semi-closed cell separation device (Elutra, Gambro BCT) that allows the collection of cells based primarily on size. This system offers obvious advantages including the automated removal of platelets and red blood cells, collection of a large number of enriched cell populations for autologous treatment including monocytes for generation of DCs, and lymphocytes for activation of T cells and LCM. Using a program developed for monocyte collection; we were able to collect upstream fractionated products containing predominantly lymphocytes. Designated as Fractions 2 and 3, these cells were cryopreserved for LCM preparation and testing. Cell profiles of each fraction of each donor were generated by flow cytometry. Cells were activated with either anti-CD3 antibody+ionomycin or anti-CD3/CD28 beads. The media was tested for cytokine composition and its capacity to 'mature' dendritic cells (DCs) and augment T cell responses.

Because this study involved the injection to humans of activated cell products, prior to any laboratory studies, the acceptability of culture materials was first determined by enquiry with FDA. It was recommended that GMP-produced serum-free media filed in previous IND's be used; and all media 'components' (including cytokines) be well-defined.

Data: Characterization of Apheresis Products Pre- and Post-Elutriation.

The cell number in healthy donor leukapheresis products and lymphocyte recoveries is shown in Table 6.

TABLE 6

| | mean ± SD* |
|---|---|
| Pre-elutriation | |
| Total MNC in product ($\times 10^9$) | 7.2 ± 3 |
| Total RBC in product ($\times 10^{10}$) | 4.3 ± 1.1 |
| Total lymphocytes in product ($\times 10^9$) | 5.6 ± 2.2 |
| Total monocytes in product ($\times 10^9$) | 1.2 ± 0.38 |
| HCT (%) | 2.2 ± 0.5 |
| Total PLT in product ($\times 10^{11}$) | 2.7 ± 0.9 |
| Percentage of lymphocytes in product | 79.3 ± 2.9 |
| Post-elutriation | |
| Cell recovery in lymphocyte-rich fraction[a] | Fraction 2: ~63%; Fraction 3: ~42% |
| Lymphocyte purity[b] | 81-86 ± 3% |

*n = 9;
[a]Percentage of cells recovered in lymphocyte-rich fractions 2 and 3 with respect to cell counts in starting material (manual count)
[b]Percentage of lymphocytes in lymphocyte-rich fraction determined by CD3+ labling Phenotype of Fraction 2 and 3 Cells To verify that the majority of cells in fractions 2 and 3 were lymphocytes, fresh and cryopreserved fractionated cells were phenotyped by labeling with fluorochrome-conjugated monoclonal antibodies against leukocyte cell surface markers. Profiles of cryopreserved cells are shown in Table 7 as in practice stored cells will be used to generate the batches of clinical product.

TABLE 7

Phenotype of Thawed elutriated fractions

| | Fraction 2* | | Fraction 3** | |
|---|---|---|---|---|
| | AVE | SD | AVE | SD |
| Viability | 87 | 7 | 88 | 15 |
| $CD45^+$ | 97 | 2 | 97 | 3 |
| $CD3^+$ | 86 | 3 | 81 | 3 |
| $CD4^+$ | 41 | 5 | 48 | 10 |
| $CD8^+$ | 29 | 6 | 21.8 | 7 |
| $CD4^+DR^+$ | 8 | 2 | 10 | 2 |
| $CD4^+CD25^+$ | 5 | 0.5 | 6 | 1 |
| $CD25^+$ | 7 | 1 | 9 | 3 |
| $CD3^+CD56^+$ | 16 | 6 | 19 | 9 |
| $CD3^-CD56^+$ | 7 | 5 | 8 | 5 |

TABLE 7-continued

Phenotype of Thawed elutriated fractions

| | Fraction 2* | | Fraction 3** | |
|---|---|---|---|---|
| | AVE | SD | AVE | SD |
| CD56+ | 23 | 10 | 24 | 16 |
| CD19+ | 3 | 1 | 4 | 2 |

FACScan analysis,
*n = 87 (storage time 9-547 days);
**n = 45 (storage time = 9-399 days)

Cytokine Composition of LCM Derived from Fractions 2 and 3

Culture conditions based on historical data in flasks and plates (Table 8) were tested with fractions 2 and 3 to select the 'best' conditions for further clinical process development.

TABLE 8

Culture conditions tested (37° C., humidified, 5% $CO_2$)
Table 6:
Culture

| | Fraction 2 | | Fraction 3 | |
|---|---|---|---|---|
| CD3-CD28 beads | X | X | X | X |

| | incubation time | | | |
|---|---|---|---|---|
| | 48 h | 72 h | 48 h | 72 h |
| No beads | X | — | X | — |
| CD3-CD28 beads + IL2 | — | X | — | X |
| No beads + IL2 | — | X | — | — |
| Anti-CD3 coating | — | X | — | — |

LCM supernatants were collected by centrifugation and stored at 4° C. until assayed. Cytokines were assessed within a single assay for direct comparison using flow cytometry-based technology (BioRad, BD Biosciences) (see Table 7).

Comment: Data suggest that anti-CD3/CD28 stimulation provide a 'manufacturing' system which is easy to execute and yields fairly consistent cytokine patterns. The use of beads compared to flask/bag surface coating with antibody may be preferred as beads can be systematically measured, their use subject to less operator error, and 'generally' similar cytokine patterns are observed.

Tables 9A and 9B show survey assay on cultures in traditional polystyrene plates or flasks.

TABLE 9A

Activation of FRACTION 2 cells
Cytokines Produced from Cells Stimulated under Different Conditions (27-Bioplex)
(pg/ml)

| | CD3-CD28 beads | No beads | CD3-CD28 beads | CD3-CD28 beads + IL2 | No beads + IL2 | Anti-CD3 Ab coating |
|---|---|---|---|---|---|---|
| | 48 h stimulation (n = 2) | | 72 h stimulation (n = 2) | | | |
| Eotaxin | 145 ± 22 | 7 ± 10 | 138 ± 60 | 487 ± 260 | 18 ± 24 | 147 ± 94 |
| FGF | 39 ± 2 | 0 ± 0 | 76 ± 43 | 162 ± 132 | 0 ± 0 | 23 ± 32 |
| G-CSF | 16.7 ± 3 | 0 ± 0 | 27 ± 11 | 89 ± 51 | 1 ± 1 | 26 ± 16 |
| GM-CSF | 1124 ± 140 | 20 ± 23 | 3551 ± 2115 | 5944 ± 2657 | 60 ± 52 | 1373 ± 961 |
| IFNγ | 42512 ± 13867 | 0 ± 0 | 50335 ± 56228 | 42997 ± 24322 | 227 ± 60 | 55600 ± 49000 |
| IP10 | 86034 ± 39358 | 254 ± 360 | 170543 ± 400405 | 13066 ± 2666 | 694 ± 327 | 1183 ± 1006 |
| IL1β | 24 ± 2 | 0.6 ± 0.1 | 21 ± 15 | 130 ± 81 | 14 ± 24 | 34 ± 10 |
| IL1ra | 164 ± 109 | 92 ± 118 | 232 ± 195 | 320 ± 143 | 140 ± 76. | 45.5 ± 10 |
| IL2 | 7944 ± 1549 | 0 ± 0 | 6750 ± 4760 | 24724 ± 9572 | 10867 ± 1961 | 5836 ± 3686 |
| IL4 | 155 ± 39 | 0 ± 0 | 292 ± 320 | 251 ± 123 | 8.2 ± 11.3 | 61 ± 47 |
| IL5 | 236 ± 225 | 0 ± 0 | 423 ± 403 | 493 ± 188 | 1.5 ± 0.6 | 183 ± 103 |
| IL6 | 1646 ± 526 | 12.9 ± 18.2 | 2797 ± 3566 | 2032 ± 670 | 18 ± 21 | 226 ± 155 |
| IL7 | 0.8 ± 0.8 | 0.0 ± 0 | 4.20 ± 2.8 | 5.00 ± 4.8 | 0 ± 0 | 0.50 ± 0.7 |
| IL8 | 2205 ± 1700 | 283 ± 350 | 4892 ± 8372 | 2197 ± 561 | 815 ± 37 | 1408 ± 1092 |
| IL9 | 1590 ± 1601 | 15 ± 18 | 1918 ± 2235 | 2523 ± 1007 | 0 ± 0 | 118 ± 167 |
| IL10 | 7298 ± 2236 | 0 ± 0 | 2122 ± 2349 | 2289 ± 629 | 0 ± 0 | 1385 ± 1033 |
| IL12 | 3 ± 1 | 0 ± 0 | 16 ± 14 | 0 ± 0 | 0 ± 0 | 0 ± 0 |
| IL13 | 874 ± 534 | 0 ± 0 | 1479 ± 772 | 1574 ± 370 | 3 ± 3 | 530 ± 160 |
| IL15 | 3 ± 0.4 | 2 ± 0.1 | 3 ± 2 | 10 ± 21 | 1.5 ± 3 | 0 ± 0 |
| IL17 | 481 ± 70 | 0 ± 0 | 1087 ± 1860 | 386 ± 293 | 0 ± 0 | 25 ± 35 |
| MCP1 | 36 ± 36 | 26 ± 37 | 69 ± 74 | 70 ± 80 | 0 ± 0 | 6 ± 8 |
| MIP1α | 21945 ± 0 | 15 ± 15 | 17781 ± 6324 | 19153 ± 0 | 413 ± 98 | 6146 ± 6832 |
| MIP1β | 13684 ± 13363 | 812 ± 646 | 18277 ± 7656 | 48070 ± 49740 | 7079 ± 2396 | 17893 ± 7504 |
| PDGFbb | 267 ± 41 | 0 ± 0 | 189 ± 169 | 779 ± 586 | 28 ± 33 | 122 ± 172 |
| RANTES | 15101 ± 182 | 322 ± 82 | 34432 ± 29650 | 7969 ± 11890 | 781 ± 33 | 1338 ± 709 |
| TNFα | 3457 ± 1540 | 0 ± 0 | 7540 ± 8717 | 7142 ± 2016 | 0 ± 0 | 2631 ± 1052 |
| VEGF | 136 ± 81 | 0 ± 0 | 242 ± 173 | 582 ± 478 | 22 ± 0 | 117 ± 132 |

TABLE 9B

Activation of FRACTION 3 cells
Cytokines Produced under Different Culture Conditions
(pg/ml)

| | CD3-CD28 beads 48 h stimulation (n = 2) | No beads | CD3-CD28 beads 72 h stimulation (n = 2) | CD3-CD28 beads + IL2 |
|---|---|---|---|---|
| Eotaxin | 173 ± 21 | 12 ± 17 | 225 ± 9 | 0 ± 0 |
| FGF | 38 ± 1 | 3 ± 4 | 56 ± 15 | 0 ± 0 |
| G-CSF | 22 ± 0.52 | 0 ± 0 | 33 ± 5 | 0 ± 0 |
| GM-CSF | 2279 ± 746 | 22 ± 1 | 5577 ± 1278 | 4 ± 6 |
| IFNγ | 223663 ± 20006 | 14 ± 21 | 327345 ± 41111 | 0 ± 0 |
| IP10 | 21221 ± 5076 | 884 ± 459 | 31794 ± 684 | 1680 ± 1073 |
| IL1β | 45 ± 3 | 1 ± 0.97 | 67 ± 24 | 1 ± 0.94 |
| IL1ra | 1969 ± 180 | 1397 ± 172 | 2715 ± 1086 | 1545 ± 495 |
| IL2 | 5518 ± 1387 | 0 ± 0 | 2655 ± 1569 | 0 ± 0 |
| IL4 | 267 ± 124 | 0 ± 0 | 252 ± 50 | 0 ± 0 |
| IL5 | 411 ± 322 | 0 ± 0 | 542 ± 273 | 0 ± 0 |
| IL6 | 1840 ± 394 | 40 ± 50 | 2378 ± 75 | 35 ± 45 |
| IL7 | 0.9 ± 0.9 | 0.05 ± 0.07 | 2 ± 0.08 | 0 ± 0 |
| IL8 | 26859 ± 13919 | 9081 ± 883 | 36702 ± 0 | 17269 ± 11218 |
| IL9 | 3437 ± 2136 | 43 ± 3 | 9363 ± 4575 | 43 ± 25 |
| IL10 | 8554 ± 973 | 0 ± 0 | 10940 ± 2529 | 0 ± 0 |
| IL12 | 27 ± 11 | 0 ± 0 | 23 ± 5 | 0 ± 0 |
| IL13 | 977 ± 574 | 0 ± 0 | 1938 ± 697 | 0 ± 0 |
| IL15 | 4 ± 0.8 | 2 ± 0.2 | 6 ± 0.9 | 2 ± 0.01 |
| IL17 | 1928 ± 200.8 | 0 ± 0 | 2860 ± 1255 | 0 ± 0 |
| MCP1 | 689 ± 94.6 | 243 ± 87 | 936 ± 308 | 222 ± 177 |
| MIP1α | 12242 ± 13722 | 48 ± 65 | 21945 ± 0 | 3 ± 4 |
| MIP1β | 13922 ± 16298 | 822 ± 583 | 15449 ± 14138 | 501 ± 443 |
| PDGFbb | 227 ± 14.6 | 0 ± 0 | 581 ± 96 | 0 ± 0 |
| RANTES | 8405 ± 944 | 111 ± 22 | 34085 ± 14533 | 93 ± 2.4 |
| TNFα | 7015 ± 770 | 0 ± 0 | 18531 ± 6916 | 0 ± 0 |
| VEGF | 176 ± 90.2 | 0 ± 0 | 277 ± 40 | 0 ± 0 |

Development of LCM Closed 'Manufacturing' Process

There appeared to be no large differences in cellular composition between fractions 2 and 3; however, cell recovery was highest in fraction 2. Fraction 2 cells were selected for further analysis and development in a closed system. A 3-day culture period using anti-CD3-CD28 bead stimulation was selected. Closed FEP VueLife® bags (2 PF-0025, American Fluoroseal Corporation, Gaithersburg, Md.) were used (in part based on our previous DC culture IND work) as they: reduce risk of contamination while allowing easy access to cells; are transparent so cells can be easily monitored; are non-reactive, i.e., no plasticizers, leachables or extractables to affect cell culture; are manufactured to meet FDA approval; allow $O_2$, $CO_2$, and $N_2$ gas transfer. FEP is impermeable to water and allows incubation without water loss; and therefore, there is no need to use humidified chambers which often is a source of contamination;

Five different aphereses from different donors were used to make LCM in a bag system. Cells were cultured in serum-free, phenol-red free XVIVO10 (BioWhittaker) media using syringe loading at $1\times10^6$ cells/ml in 15 ml media plus CD3-CD28 beads (Dynabeads, Dynal) at 3 beads to 1 cell. Bags were placed atop wire racks to ensure proper gas exchange and even cell distribution then incubated for 3 days at 37° C.

Following culture, cells and LCM from individual units were collected by removing beads with a Dynal magnet followed by centrifugation (10 min at 400×g). Cells were phenotyped (Table 10) and collected supernatants were assayed for cytokines using 27 Bioplex flow-based analyses (Table 11 A, B).

Characterization of Activation Products Produced in Closed System

TABLE 10

Phenotype of elutriated cells following activation*

| | CD3-CD28 activated | | Non-activated (i.e., no beads but cells in culture) | |
|---|---|---|---|---|
| | AVE | SD | AVE | SD |
| Viability | 80 | 4 | 91 | 6 |
| CD3+ | 76 | 7 | 73 | 6 |
| CD4+ | 42 | 6 | 36 | 9 |
| CD8+ | 39 | 18 | 32 | 9 |
| HLA-DR+ | 20 | 16 | 14 | 5 |
| CD25+ | 71 | 9 | 1 | 1 |
| CD19+ | 7 | 7 | 10 | 4 |

Cytokines Released from Activated Cells

TABLE 11A

Cytokines found in supernatants from lymphocyte cultures in 'bag' system*
CD3-CD28 bead activation

| | Apheresis unit (pg/ml) | | | | | N = 5 |
|---|---|---|---|---|---|---|
| | APH062805 | APH082305 | APH112905 | APH011006 | APH112706 | Ave ± SD |
| Eotaxin | 78 | 86 | 132 | 160 | 117 | 115 ± 34 |
| FGF | 79 | 95 | 117 | 134 | 115 | 108 ± 21 |
| G-CSF | 18 | 21 | 31 | 41 | 31 | 29 ± 9 |
| GM-CSF | 3409 | 3619 | 3595 | 8189 | 3446 | 4452 ± 2091 |
| IFNγ | 5240 | 7474 | 27957 | 188081 | 54453 | 56641 ± 76098 |
| IP10 | 6158 | 9415 | 54621 | 87794 | 1234754 | 278548 ± 535605 |
| IL1β | 7 | 6 | 9 | 18 | 19 | 12 ± 6 |
| IL1ra | 115 | 117 | 160 | 659 | 396 | 289 ± 237 |
| IL2 | 3161 | 4510 | 14896 | 14896 | 6676 | 8828 ± 5680 |
| IL4 | 241 | 247 | 351 | 1108 | 254 | 440 ± 376 |
| IL5 | 425 | 358 | 328 | 1431 | 247 | 558 ± 492 |
| IL6 | 977 | 955 | 3207 | 11942 | 2852 | 3986 ± 4567 |
| IL7 | 5 | 6 | 8 | 7 | 6 | 6 ± 1 |
| IL8 | 973 | 759 | 1216 | 7404 | 26397 | 7350 ± 11006 |
| IL9 | 531 | 132 | 2040 | 6364 | 1397 | 2093 ± 2501 |
| IL10 | 469 | 302 | 591 | 2625 | 1424 | 1082 ± 965 |
| IL12 | 29 | 46 | 12 | 26 | 20 | 27 ± 12 |
| IL13 | 1804 | 2718 | 737 | 2309 | 1148 | 1743 ± 813 |
| IL15 | 3 | 3 | 5 | 7 | 5 | 5 ± 2 |
| IL17 | 102 | 118 | 1855 | 5808 | 805 | 1738 ± 2385 |
| MCP1 | 37 | 24 | 44 | 138 | 242 | 97 ± 93 |
| MIP1α | 19153 | 19153 | 19153 | 19153 | 19153 | 19153 ± 0 |
| MIP1β | 23200 | 23200 | 23200 | 23200 | 9465 | 20453 ± 6143 |
| PDGFbb | 57 | 65 | 70 | 127 | 165 | 97 ± 47 |
| RANTES | 76360 | 73239 | 15223 | 64659 | 37225 | 53341 ± 26299 |
| TNFα | 2026 | 1801 | 7344 | 29476 | 9507 | 10031 ± 11373 |
| VEGF | 266 | 577 | 97 | 133 | 108 | 236 ± 202 |

*72 h incubation

TABLE 11B

Cytokines found in supernatants from lymphocyte cultures in 'bag' system*
No Beads

| | Apheresis unit (pg/ml) | | | | | N = 5 |
|---|---|---|---|---|---|---|
| | APH062805 | APH082305 | APH112905 | APH011006 | APH112706 | Ave ± SD |
| Eotaxin | 78 | 86 | 132 | 160 | 117 | 115 ± 34 |
| FGF | 79 | 95 | 117 | 134 | 115 | 108 ± 21 |
| G-CSF | 18 | 21 | 31 | 41 | 31 | 29 ± 9 |
| GM-CSF | 3409 | 3619 | 3595 | 8189 | 3446 | 4452 ± 2091 |
| IFNγ | 5240 | 7474 | 27957 | 188081 | 54453 | 56641 ± 76098 |
| IP10 | 6158 | 9415 | 54621 | 87794 | 1234754 | 278548 ± 535605 |
| IL1β | 7 | 6 | 9 | 18 | 19 | 12 ± 6 |
| IL1ra | 115 | 117 | 160 | 659 | 396 | 289 ± 237 |
| IL2 | 3161 | 4510 | 14896 | 14896 | 6676 | 8828 ± 5680 |
| IL4 | 241 | 247 | 351 | 1108 | 254 | 440 ± 376 |
| IL5 | 425 | 358 | 328 | 1431 | 247 | 558 ± 492 |
| IL6 | 977 | 955 | 3207 | 11942 | 2852 | 3986 ± 4567 |
| IL7 | 5 | 6 | 8 | 7 | 6 | 6 ± 1 |
| IL8 | 973 | 759 | 1216 | 7404 | 26397 | 7350 ± 11006 |
| IL9 | 531 | 132 | 2040 | 6364 | 1397 | 2093 ± 2501 |
| IL10 | 469 | 302 | 591 | 2625 | 1424 | 1082 ± 965 |
| IL12 | 29 | 46 | 12 | 26 | 20 | 27 ± 12 |
| IL13 | 1804 | 2718 | 737 | 2309 | 1148 | 1743 ± 813 |
| IL15 | 3 | 3 | 5 | 7 | 5 | 5 ± 2 |
| IL17 | 102 | 118 | 1855 | 5808 | 805 | 1738 ± 2385 |
| MCP1 | 37 | 24 | 44 | 138 | 242 | 97 ± 93 |
| MIP1α | 19153 | 19153 | 19153 | 19153 | 19153 | 19153 ± 0 |
| MIP1β | 23200 | 23200 | 23200 | 23200 | 9465 | 20453 ± 6143 |
| PDGFbb | 57 | 65 | 70 | 127 | 165 | 97 ± 47 |
| RANTES | 76360 | 73239 | 15223 | 64659 | 37225 | 53341 ± 26299 |
| TNFα | 2026 | 1801 | 7344 | 29476 | 9507 | 10031 ± 11373 |
| VEGF | 266 | 577 | 97 | 133 | 108 | 236 ± 202 |

*72 h incubation

Comment: Particularly IFNγ, IP10, IL6, IL9, IL10, TNFα and the chemoattractants appear to be produced at the highest concentrations following stimulation with some variability between units. Though fraction 2 is relatively pure, variation could be possibly due to cell types (e.g., NK cells) and their proportion in each fraction.

A summary of the function of these cytokines for reference is given in Table 12. Awareness of the cytokine concentrations prior to experiments may be used to calculate actual cytokine amount in dilutions, enable matched comparisons between donors, and establish a dosing level for LCM application.

TABLE 12

Selected Cytokines and Their Activities*

| Cytokine | Producing Cell | Function |
|---|---|---|
| GM-CSF | Th cells | growth and differentiation of monocytes and DC |
| IFNγ | T cells, NK cells | antiviral, anti-tumor activity, immunoregulation; activates APCs, promotes Th1 |
| IP10 (IFNγ inducible protein) | activated T cells | mediates Ca+ mobilization, chemotaxis |
| IL-2 | Th1 cells | growth, proliferation, activation |
| IL-4 | Th2 cells | proliferation and differentiation MHC Class II proliferation |
| IL-5 | Th2 cells | proliferation and differentiation |
| IL-6 | monocytes, macrophages, Th2 cells | differentiation into plasma cells antibody secretion differentiation |
| IL-8 | macrophages, endothelial cells | chemotaxis |
| IL-10 | Th2 cells | cytokine production activation |
| IL-12 | macrophages, B cells | differentiation into CTL (with IL-2) activation MHC expression proliferation pathogen elimination |
| MIP-1α | macrophages, activated NK, CD8+T, CD4+T | chemotaxis |
| MIP-1β | activated NK, CD8+T, CD4+T | chemotaxis |
| RANTES (regulated on activation normal T cell expressed and secreted) | activated NK, CD8+T, CD4+T | chemotaxis |
| TNFα | macrophages, mast cells, NK cells | CAM and cytokine expression, cellular proliferation, differentiation, inflammation, cell death |

*derived from sources in the literature

The Effects of LCM Produced in Closed System on Autologous Monocytes/DCs

Figure 14:
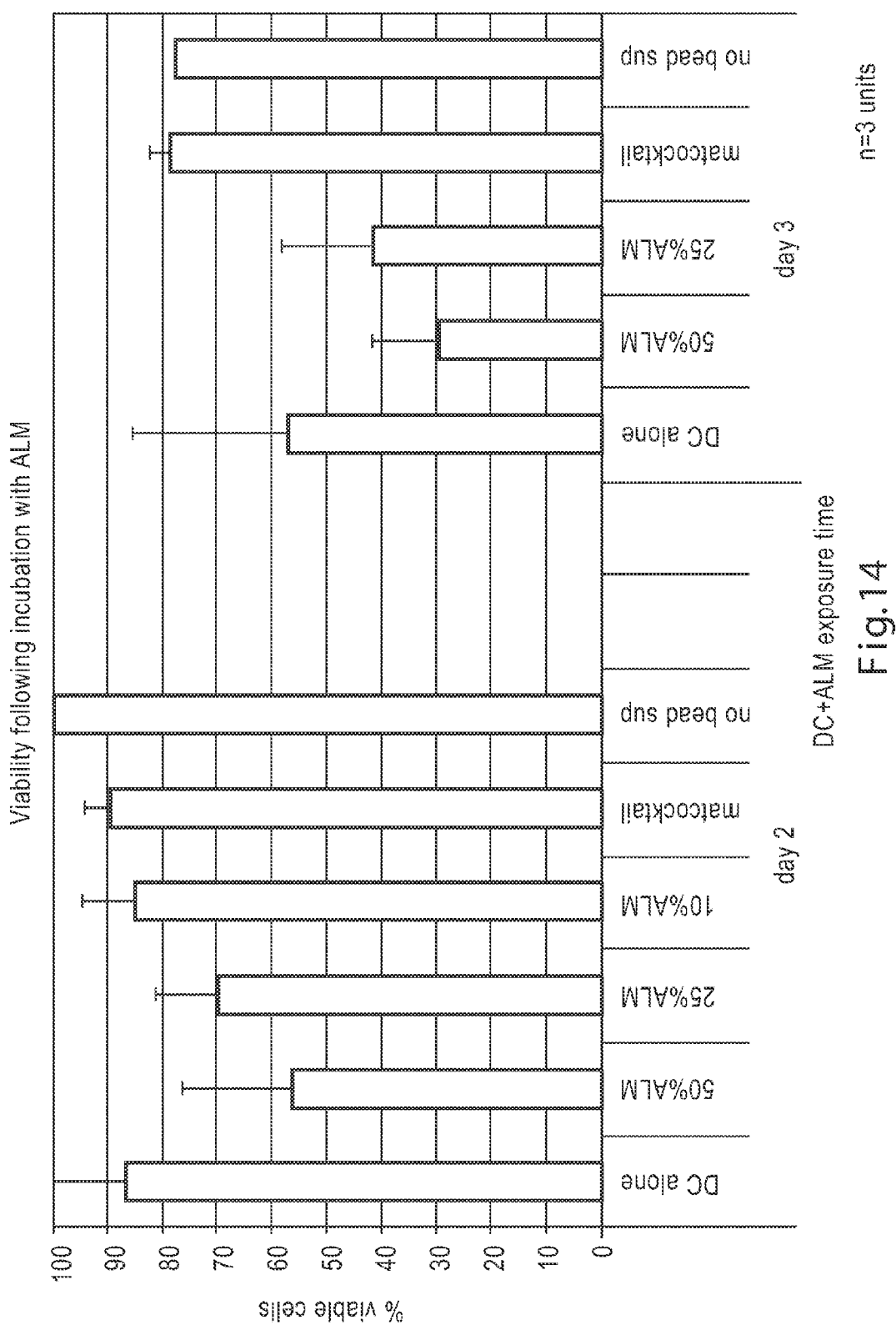
FIG. 14 shows percent viability following incubation with LCM.
Figure 15:
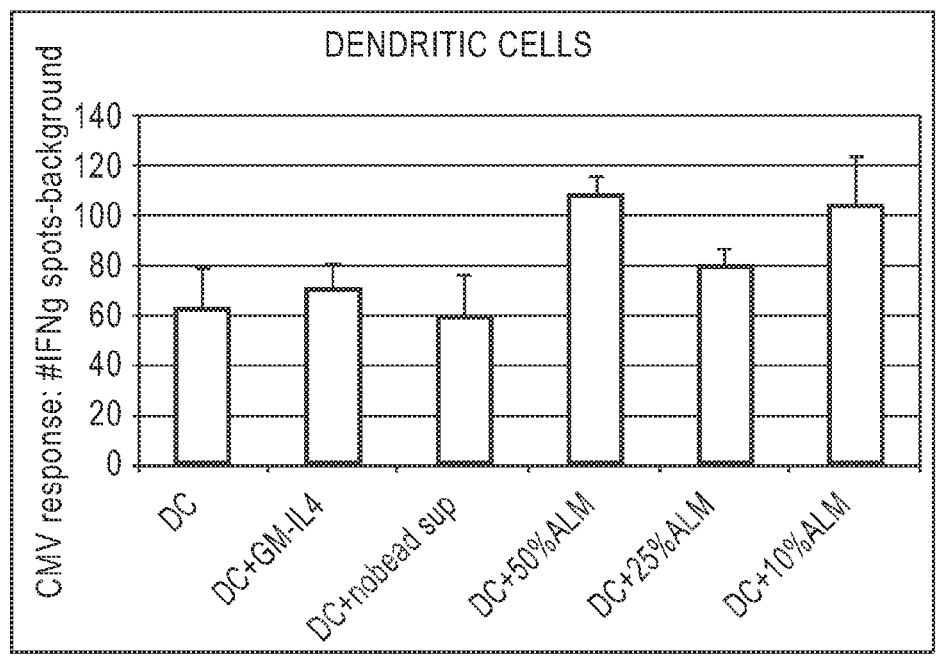
FIGS. 15 A, B provides recall responses and shows that LCM augments response to antigens (CMV, n=2); A: Aph082305 and Aph011006; B: Aph082305 and Aph011006.
Figure 15:
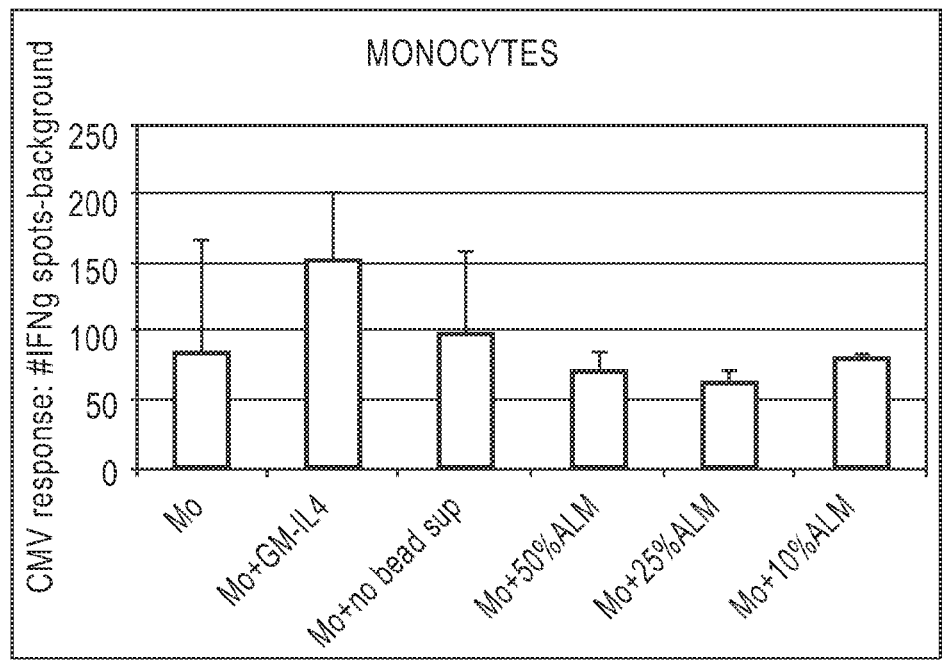
Figure 16:
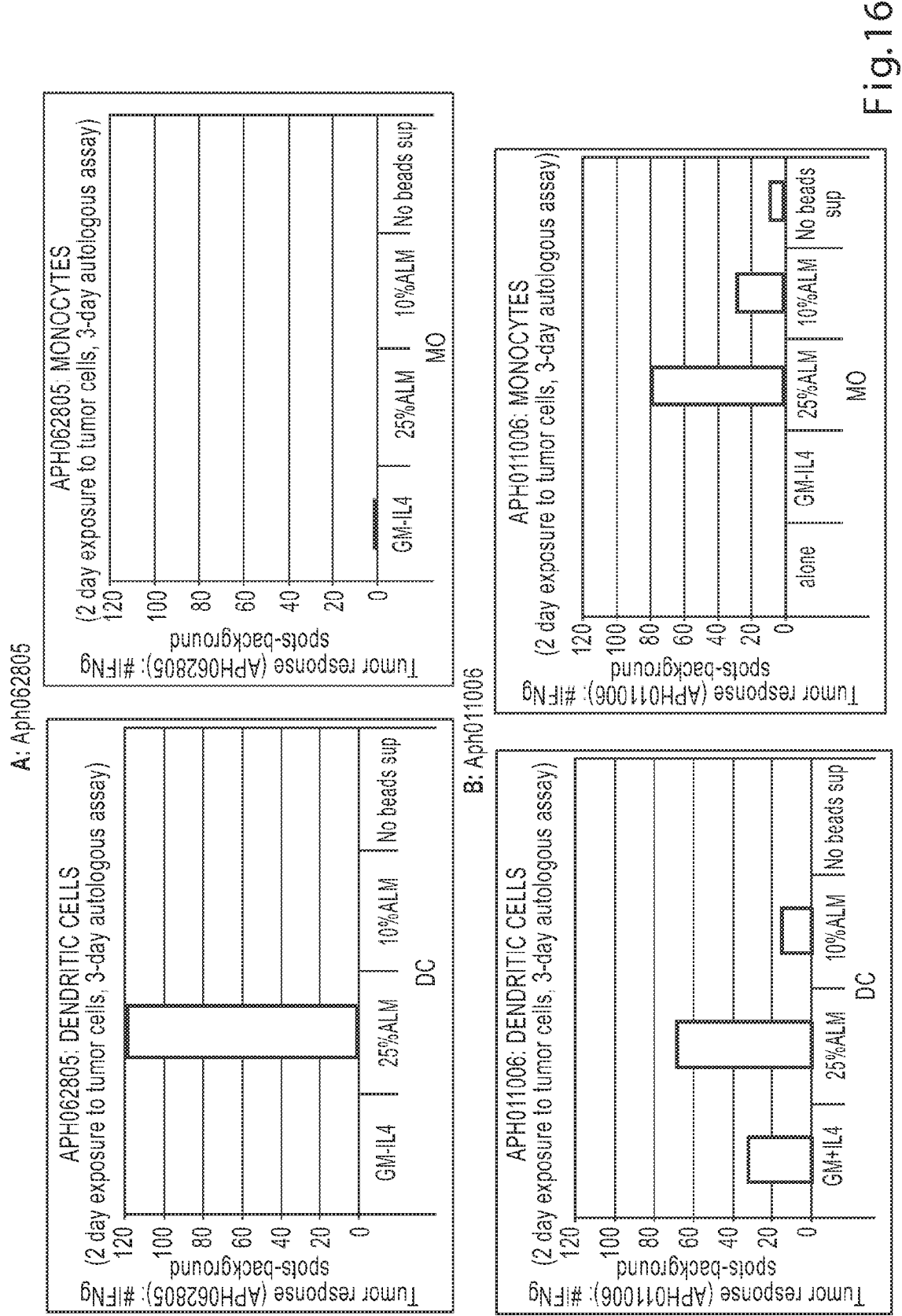
FIGS. 16 A, B shows tumor cell lysates (n=2); A: Aph062805; B: Aph011006.

To assess their properties LCM, or activated T (AT) cells, were added to autologous DCs (for 2-3 days or overnight, respectively). The autologous setting was first tested as this would be the likely protocol 'type' for immunotherapeutic approval. Treated cells were examined for: (a) viability following culture measured by trypan blue exclusion (FIG. 14); (b) changes in surface marker expression (e.g., CD14, CD40, CD80, CD83, CD86) measured by flow cytometry (Tables 13, 14); (c) effects on T cell responses measured in IFNγ ELISPOT following exposure to CMV and tumor lysates before and after IL7+IL15 expansion (FIGS. 15, 16).

Cell surface marker expression on DCs following exposure to autologous LCM is shown in Table 13.

TABLE 13

| | % expression | | | | |
|---|---|---|---|---|---|
| | CD14 | CD40 | CD80 | CD86 | CD83 |
| pre-LCM exposure | Day 0 | | | | |
| DC (thawed, no additional cytokines added) | 20 | 77 | 74 | 86 | 2 |
| post-LCM exposure | Day 2→Day 3 | | | | |
| DC alone | 20→7 | 55→31 | 58→22 | 73→51 | 4→5 |
| DC + LCM (50%) | 9→23 | 47→54 | 42→30 | 54→70 | 11→16 |
| DC + LCM (25%) | 21→22 | 64→60 | 63→39 | 67→70 | 12→13 |
| DC + LCM (10%) | 22→ND | 52→ND | 49→ND | 49→ND | 13→ND |
| DC + non-activated (i.e., no bead) medium | 4→40 | 42→44 | 35→36 | 19→51 | 6→5 |
| DC + maturation cocktail (IL1β, IL6, TNFα, PGE2) | 43→56 | 64→54 | 56→52 | 66→63 | 27→15 | n = 3 units;
ND = not determined

Table 14 shows cell surface marker expression on DCs* following overnight exposure to autologous activated T cells.

TABLE 14

| Culture Condition | Donor | Viability | Marker (% expression) | | | | |
|---|---|---|---|---|---|---|---|
| | | | CD14 | CD40 | CD80 | CD83 | CD86 |
| DCs pre-coculture | APH112706 | 93 | 38 | 79 | 86 | 1 | 98 |
| | APH082305 | 98 | 2 | 70 | 80 | 0 | 42 |
| DCs + non-activated T cells | APH112706 | 57 | 31 | 92 | 92 | 78 | 65 |
| | APH082305 | 84 | 12 | 98 | 94 | 95 | 94 |
| DCs + activated T cells | APH112706 | 63 | 5 | 27 | 12 | 4 | 43 |
| | APH082305 | 85 | 0 | 83 | 94 | 77 | 94 |

*Gating set on DCs
Refer to cytokine profiles for activation of T cells from these units (Table 9).
High IFNγ production was measured following stimulation of APH112706.
NOTE: Cytokine release assessed following coculture of DC and non-activated T cells or AT cells** showed the following

| | Culture Condition | | | |
|---|---|---|---|---|
| | DC alone | DC + AT cells | DC + non-activated T cells | T cells alone |
| Eotaxin | 36 | 63 | 0 | 1 |
| FGF | 38 | 123 | 41 | 10 |
| G-CSF | 0 | 19 | 0 | 0 |
| GM-CSF | 608 | 536 | 250 | 0 |
| IFNγ | 23 | 241 | 16 | 0 |
| IP10 | 70 | 54621 | 5256 | 71 |
| IL1β | 1 | 18 | 3 | 1 |
| IL1ra | 386 | 16394 | 730 | 0 |
| IL2 | 0 | 12 | 1 | 0 |
| IL4 | 56 | 45 | 31 | 0 |
| IL5 | 1 | 10 | 1 | 1 |
| IL6 | 25 | 421 | 152 | 45 |
| IL7 | 4 | 15 | 0 | 0 |
| IL8 | 248 | 18225 | 2542 | 137 |
| IL9 | 5 | 58 | 6 | 0 |
| IL10 | 2 | 11 | 2 | 0 |
| IL12 | 5 | 4 | 0 | 0 |
| IL13 | 0 | 329 | 0 | 0 |
| IL15 | 1 | 2 | 1 | 0 |
| IL17 | 20 | 82 | 31 | 23 |
| MCP1 | 8 | 288 | 44 | 0 |
| MIP1α | 4 | 39 | 9 | 16 |
| MIP1β | 69 | 821 | 507 | 261 |

TABLE 14-continued

| PDGFbb | 29 | 849 | 122 | 34 |
|---|---|---|---|---|
| RANTES | 9 | 1125 | 319 | 673 |
| TNFα | 16 | 243 | 23 | 14 |
| VEGF | 85 | 87 | 20 | 13 |

**APH082305; sups from other cocultures have been stored and are available to assay Comment: DCs incubated with LCM (for 2 or 3 days) demonstrate some upregulation in the maturation marker CD83, as well as changes in costimulatory molecule expression. When autologous activated or non-activated T cells are added (overnight) to DCs in another set of wells, as expected, upregulation of costimulatory markers is observed in both cell populations-except with AT cells from donor APH112706, which showed a negative change in costimulatory molecules. Though difficult to make sweeping statements with such low sample sizes, these changes could be attributable to a number of factors including level of stimulation, receptor activation on T cells, cytokines and or viable status. Viability may not be the issue here as non-activated T cell-DC samples demonstrated equal viability with maintained high DC marker expression. The 'stimulatability' of T cells from donor APH112706 shows that CD3-CD28-activation can produce high levels of IFNγ (see Table 9a) which is APC activating and our observation could be due to high activation and 'spent' status which occurred prior to our measurement point.

Cytokines released from DC-T cell cocultures underscore the importance of activation levels (IFNγ and chemotactic cytokines). With the addition of antigen and expanded observation points, these measures may prove useful to further characterize and screen individual cells for activation status and potential clinical efficacy, particularly if indicative of differences between induction of immunity or tolerance.

Recall and Primary T Cell Responses-ELISPOT
Description
1. Supernatants and antigen were added to monocytes and DCs (designated as APC):
   i. Source of DCs: cryopreserved/cultured from monocytes (3 days, serum-free DC medium (CellGenix, Germany) GM-CSF (800 IU/ml)+IL4 (500 IU/ml) (CellGenix);
   ii. Source of monocytes: cryopreserved elutriated rotor-off fraction;
   iii. Cell supernatants tested: 50%, 25% and 10% of original strength from CD3-CD28 bead-activated or non-activated cells;
2. Cultures were incubated for 2 days at 37° C. and washed free or LCM or non-activated supernatants then placed in IFNγ ELISPOT assay (see schematic below):
   a. For recall responses:
      i. cells were counted; autologous lymphocytes (fraction 2) were added at 10 lymphocytes: 1 APC (total $1.5 \times 10^5$ cells/well) then
      ii. plated on IFNγ antibody-coated ELISPOT plates, incubated for 3 days at 37° C. then plates developed and enumerated
   b. For primary responses:
      i. Washed cells were cultured in IL7+IL15 (5 ng/ml each) for 7 days, then washed and plated on coated ELISPOT plates and developed as above.

Table 15 is a schematic of the assay.

TABLE 15

Schematic of Assay

| Day 0 | Day 2 | Day 8 | Day 9 | Culture Conditions DCs and monocytes |
|---|---|---|---|---|
| Culture DCs and monocytes: ±LCM ±tumor (myeloma 8226)($3 \times 10^4$ cell equivalent lysate per well or CMV lysate (0.01 mg/well) | Harvest APCs, wash and add T cells: RECALL: Assay portion cells in ELISPOT PRIMARY: Expand portion of cells in IL7 + IL15 for 7 days | Restimulate cells with antigen or Add antigen to antigen-naive cells overnight | Harvest cells and assay in ELISPOT IFNγ | alone +GM-IL4 +25% LCM +10% LCM +no bead sup +tumor lysate (d0 + d8 or d8) +GM-IL4 + tumor lysate (d0 + d8 or d8) +25% LCM + tumor lysate (d0 + d8 or d8) +10% LCM + tumor lysate (d0 + d8 or d8) +no bead sup + tumor lysate (d0 + d8 or d8) |

Results

FIGS. 15 A, B provides recall responses and shows that LCM augments response to antigens (CMV, n=2).

FIGS. 16 A, B shows tumor cell lysates (n=2), in which FIG. A is Aph062805 and FIG. B is Aph-11006.

Comment: Cocultures of either DC preparation with LCM and tumor cells show enhanced T cell responses; however, the response is larger in cultures from donor APH011006 compared to donor APH062805. It is interesting to refer to the cytokine table (Table 9) and compare the differences in the degree of the capacity for IFNγ production following activation between the donors. Though different levels in the number of spots in this type of assay are expected, in vivo potential may be predictable by determining a stimulation index for a particular cytokine. Such an index would prove useful for screening potential positive activity; however, to determine if this is a real response, a larger sample evaluation to include appropriate controls will be necessary. Interestingly, the monocyte-antigen cocultures in donor APH011006 also show a larger response than those in the APH062805 donor (FIG. 16B) possibly due to the capacity for detection of IFNγ in this donor or activity of other cytokines such as TNFγ. Higher TNFγ levels were also present in the LCM of this donor which could 'push' the monocyte to a DC. Unfortunately, the phenotype of these cells was not determined due to limited amount of material.

These data warrant future study to determine the cell (maturation) status and how the cytokine levels should be manipulated to control and potentially predict function.

Primary Responses: IL7-IL15 T Cell Expansion

Figure 17:
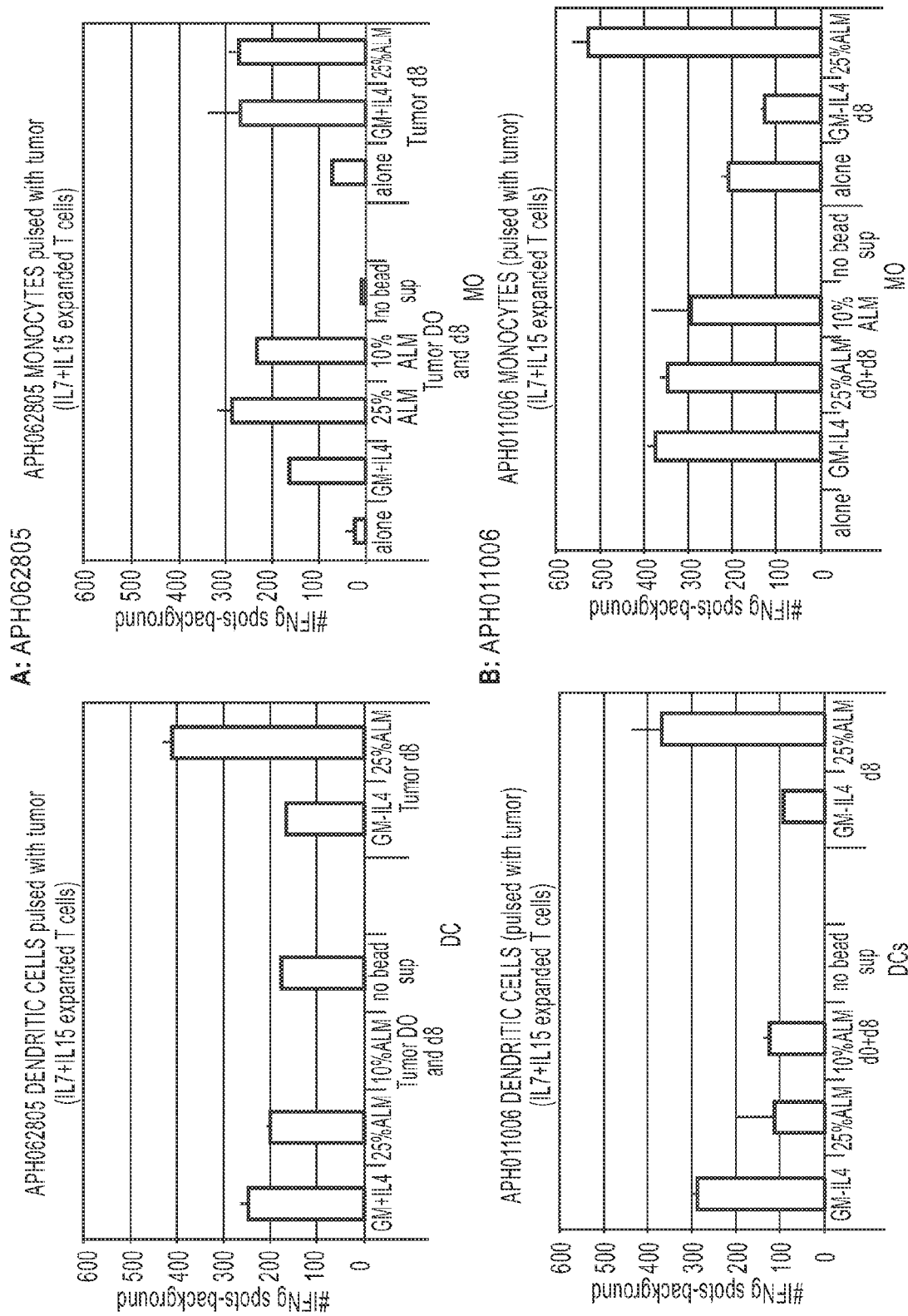
FIGS. 17 A, B shows responses of LCM-treated 'naïve IL7-IL15-treated' cells (N=2); A: Aph062805; B: Aph01106.

FIG. 17 shows responses of LCM-treated 'naïve IL7-IL15-treated' cells (i.e., cells first exposed to tumor on day 8) were enhanced compared to cells exposed to antigen on days 0 and 8.

Comment: LCM added to DCs and monocytes enhanced tumor antigen presentation to antigen-naïve T cells cultured in IL7 and IL15 for 7 days prior to antigen stimulation. The higher response levels compared to short recall responses (FIG. 15) could be due to the cytokines that help to maintain viability of T or APCs (cell viability 78-100%). When IL7 and IL15 antigen-treated expanded cultures were restimulated with antigen, that is, pulsed with antigen both on days 0 and 8, there was a response in LCM-treated APCs above non-treated; however, the responses were lower than that of APCs that had been treated with GM-IL4. The LCM data may indicate the presence of suppressive factors or optimal levels of cytokine were present-absent and should be adjusted. This data is reported from two different donors. Expanded studies would be valuable to better characterize the responding cells functionally and phenotypically.

Though it may appear that using a few cytokines would be 'easiest' to generate a desired immune response, it may be that the mix of cytokines found in LCM will be the most potent; mimicking a true physiological response and demonstrating that cytokine interactions are essential in optimizing functional activity.

SUMMARY

In this protocol, elutriated fractions 2 or 3 may be used for activation. The greatest number of lymphocytes were collected in fraction 2 (Table 6). There were fairly consistent results between the two fractions (Table 9); however, purity in fraction 3 may be an issue if cell levels in the starting units do not meet optimal elutriation criteria. That is, if the starting total cell number (i.e., $\geq 5 \times 10^9$ cells) or monocyte count (i.e., $\geq 1 \times 10^9$) falls below the recommended level for the cell separator, cell fractionation patterns can shift and result in heterogeneous cell distribution in later fractions.

Fractionated or lymphocyte-enriched cell populations permit 'controlled' activation as measured by the composition of cell products in the LCM. Cytokines, particularly GM-CSF, IFNγ, IP10, IL2, IL6, IL8, IL9, IL10, IL13, MIP1α, MIP1β, RANTES, TNFα, were most highly induced at fairly even distributions (Table 13); however, more samples should be evaluated for presentation to FDA.

LCM enhanced the expression levels of costimulatory molecules (e.g., CD40, CD80, CD86, and CD83) on DCs, an indication of the maturation process important to antigen presentation (Table 13).

LCM promoted an 'adjuvant-like' effect on DC function. DCs treated in vitro with 50-25% of the original LCM solution were able to stimulate responses to CMV and tumor antigens in recall assays (FIG. 15).

LCM may help APC function and expand antigen-specific T cells (FIG. 16); however, optimal levels of cytokine are currently undefined (Note: compare to cells incubated with the 'standard' GM-CSF+IL4 formulation).

Based on preliminary results, elutriated cells appear to be a good source for the preparation of LCM in the autologous setting. Note PBMC preparations and elutriated fractions were not directly compared from the same donors in "side-by-side" studies. Stimulated PBMCs, presumably due to the presence of monocytes or possibly platelets, do appear to express some cytokines (e.g., MCP1) not seen at high levels in the elutriated cells which could endow a more robust adjuvant effect.

Further development of the production of LCM or cells is warranted, in which a closed system design illustrated in FIG. 17 could be applied to clinical use.

Figure 18:
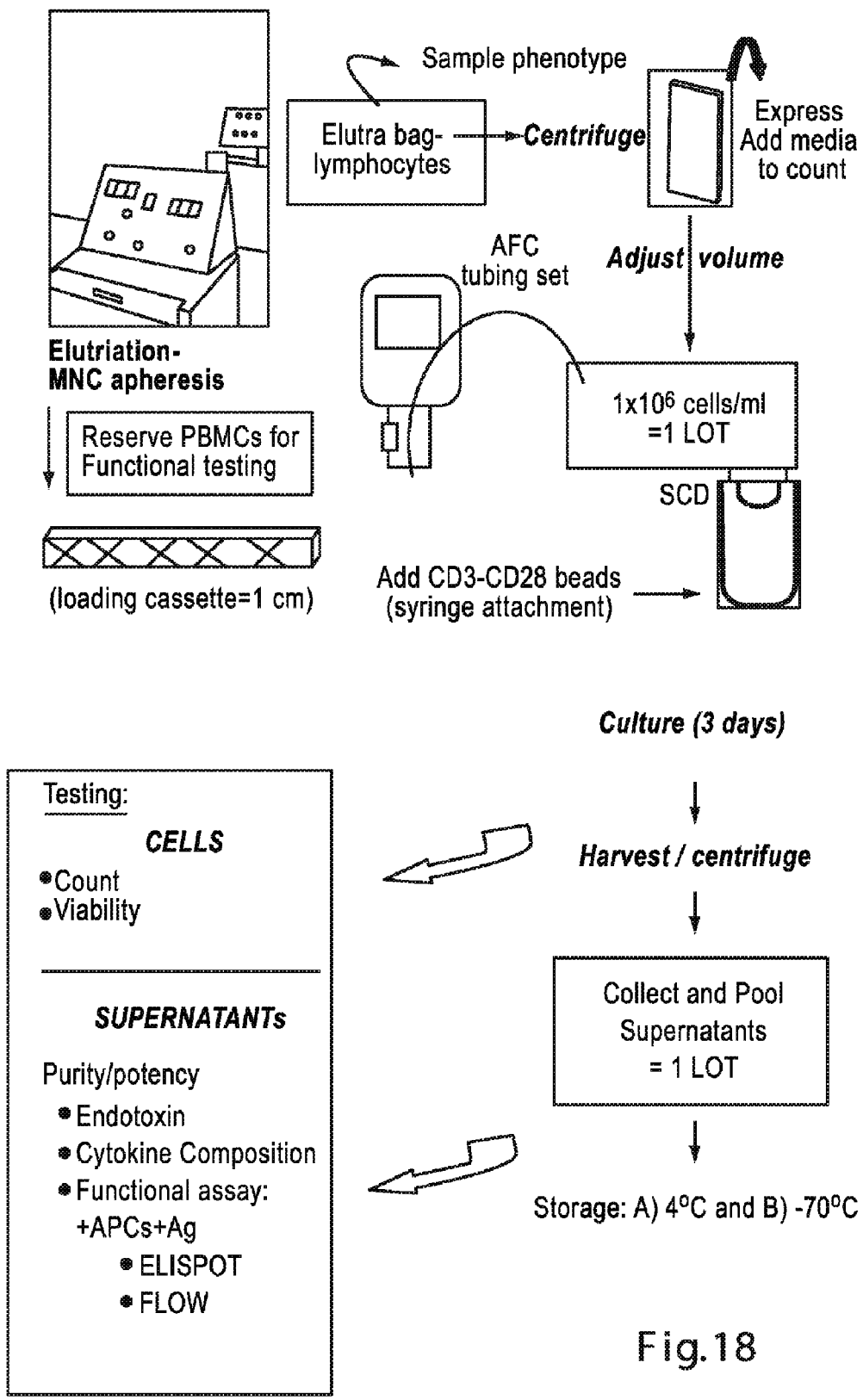
FIG. 18 shows a proposed culture system for lymphocytes.

FIG. 18 shows a proposed culture system for lymphocytes.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of stabilizing or regressing a tumor in a patient comprising the steps of:
   collecting monocyte cells from the patient afflicted with the tumor, said tumor selected from the group consisting of gastric carcinoma, epipharyngial carcinoma, sigmoid carcinoma, melanoma, rectal carcinoma, breast carcinoma, pelvic carcinoma, endometrial carcinoma, and mesothelioma;
   culturing the monocyte cells with IL-4 and GM-CFS to form immature dendritic cells from the monocyte cells;
   combining the immature dendritic cells and a leukocyte cultured medium adjuvant to form a composition, said leukocyte cultured medium adjuvant comprising at least three cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF; and
   administering intratumorally a therapeutically effective amount of the composition to the patient.

2. The method according to claim 1, wherein said LCM adjuvant comprises at least six cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF.

3. The method according to claim 2, wherein said LCM adjuvant comprises at least ten cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF.

4. The method of claim 1, wherein the patient is a human.

5. The method of claim 1, further comprising the step of treating the patient with chemotherapy prior to the administration of the immature dendritic cells and LCM adjuvant.

6. The method of claim 1, further comprising the step of treating the patient with radiation therapy prior to administration of the immature dendritic cells and LCM adjuvant.

7. A method of stabilizing or regressing a tumor in a patient comprising the steps of:
   collecting monocyte cells from the patient afflicted with the tumor, said tumor selected from the group consisting of gastric carcinoma, epipharyngial carcinoma, sigmoid carcinoma, endometrial carcinoma, pelvic carcinoma, mesothelioma, melanoma, rectal carcinoma, and breast carcinoma;
   culturing the monocyte cells with IL-4 and GM-CFS to form immature dendritic cells from the monocyte cells;
   combining the immature dendritic cells and a leukocyte cultured medium adjuvant to form a composition, said leukocyte cultured medium adjuvant comprising at least three cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF;

administering chemotherapy to the patient; and administering intratumorally a therapeutically effective amount of the composition to the patient.

8. The method according to claim 7, wherein said LCM adjuvant comprises at least six cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF.

9. The method according to claim 8, wherein said LCM adjuvant comprises at least ten cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF.

10. The method of claim 7, wherein the patient is a human.

11. The method of claim 7, further comprising the step of treating the patient with radiation therapy prior to the administration of the immature dendritic cells and LCM adjuvant.

12. A method of stabilizing or regressing a tumor in a patient comprising the steps of:

collecting monocyte cells from the patient afflicted with the tumor, said tumor selected from the group consisting of gastric carcinoma, rectal carcinoma, epipharyngial carcinoma, sigmoid carcinoma, endometrial carcinoma, pelvic carcinoma, mesothelioma, melanoma, and breast carcinoma;

culturing the monocyte cells with IL-4 and GM-CFS to form immature dendritic cells from the monocyte cells;

combining the immature dendritic cells and a leukocyte cultured medium adjuvant to form a composition, said leukocyte cultured medium adjuvant comprising at least three cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF;

administering radiation therapy to the patient; and administering intratumorally a therapeutically effective amount of the composition to the patient.

13. The method according to claim 12, wherein said LCM adjuvant comprises at least six cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF.

14. The method according to claim 13, wherein said LCM adjuvant comprises at least ten cytokines selected from the group consisting of eotaxin, FGF, G-CSF, GM-CSF, IFNγ, IP10, IL1β, IL1ra, IL2, IL4, IL5, IL6, IL7, IL8, IL9, IL10, IL12, IL13, IL15, IL17, MCP1, MIP1α, MIP1β, PDGFbb, RANTES, TNFα, and VEGF.

15. The method of claim 13, wherein the patient is a human.

16. The method of claim 13, further comprising the step of treating the patient with chemotherapy at a time prior to introducing the immature dendritic cells and LCM adjuvant into the tumor tissue.

* * * * *

UNITED STATES PATENT AND TRADEMARK OFFICE
CERTIFICATE OF CORRECTION

PATENT NO. : 8,076,132 B2
APPLICATION NO. : 12/100878
DATED : December 13, 2011
INVENTOR(S) : Kenichiro Hasumi It is certified that error appears in the above-identified patent and that said Letters Patent is hereby corrected as shown below:

IN THE SPECIFICATIONS:

Column 3, line 2, "ILβ" should read --IL1β--.
Column 4, line 40, "in clude" should read --include--.
Column 4, line 50, "treatment tumor tissue" should read --treatment of tumor tissue--.
Column 6, line 56, "therapies 1." should read --therapies.--.
Column 6, line 57, "Methods" should read --1. Methods--.
Column 9, line 62, "24 hours:" should read --24 hours):--.
Column 10, TABLE 4, lines 37-38, "          Treatment            0  7  14  21  28  35  42  49  56
                                       Days of injection                "

should read

Days of injection
--          Treatment            0  7  14  21  28  35  42  49  56        --.

Column 10, TABLE 4, lines 53-54,
        PSA
     " Cells (ELISPOT) "
should read
        PSA
                       Days samples collected for testing
     -- Cells (ELISPOT)                                          --.

Column 13, TABLE 8, lines 23-24,
                           Fraction 2           Fraction 3
" CD3-CD28 beads            X      X             X      X "
should read
                         -- Fraction 2           Fraction 3 --.

Signed and Sealed this
Eighth Day of May, 2012

David J. Kappos
*Director of the United States Patent and Trademark Office*

CERTIFICATE OF CORRECTION (continued)
U.S. Pat. No. 8,076,132 B2

Column 14, above line 5, insert the following:
-- CD3-CD28 beads        X        X        X        X --.

Column 15, line 57, "combination;" should read --combination.--.